United States Patent
Jiang et al.

(10) Patent No.: US 12,194,103 B2
(45) Date of Patent: Jan. 14, 2025

(54) IMMUNOSUPPRESSIVE MATERIALS AND RELATED METHODS

(71) Applicant: University of Washington, Seattle, WA (US)

(72) Inventors: Shaoyi Jiang, Seattle, WA (US); Bowen Li, Seattle, WA (US); Priyesh Jain, Seattle, WA (US)

(73) Assignee: University of Washington, Seattle, WA (US)

( * ) Notice: Subject to any disclaimer, the term of this patent is extended or adjusted under 35 U.S.C. 154(b) by 986 days.

(21) Appl. No.: 17/040,455

(22) PCT Filed: Mar. 25, 2019

(86) PCT No.: PCT/US2019/023921
§ 371 (c)(1),
(2) Date: Sep. 22, 2020

(87) PCT Pub. No.: WO2019/183637
PCT Pub. Date: Sep. 26, 2019

(65) Prior Publication Data
US 2021/0023228 A1    Jan. 28, 2021

Related U.S. Application Data

(60) Provisional application No. 62/647,534, filed on Mar. 23, 2018.

(51) Int. Cl.
| | |
|---|---|
| A61K 47/58 | (2017.01) |
| A61K 38/44 | (2006.01) |
| A61K 47/69 | (2017.01) |
| C07F 9/09 | (2006.01) |
| C08F 299/00 | (2006.01) |

(52) U.S. Cl.
CPC ........... *A61K 47/585* (2017.08); *A61K 38/44* (2013.01); *A61K 47/6903* (2017.08); *C07F 9/091* (2013.01); *C08F 299/00* (2013.01); *C12Y 107/03003* (2013.01)

(58) Field of Classification Search
None
See application file for complete search history.

(56) References Cited

U.S. PATENT DOCUMENTS

| | | | |
|---|---|---|---|
| 6,953,591 | B2 | 10/2005 | Bolton et al. |
| 7,850,982 | B2 | 12/2010 | Stopek et al. |
| 8,778,379 | B2 | 7/2014 | Doshi et al. |
| 9,332,755 | B2 | 5/2016 | Steinburg et al. |
| 2003/0004097 | A1 | 1/2003 | Schroit |
| 2003/0216534 | A1 | 11/2003 | Chaikof et al. |
| 2005/0208122 | A1 | 9/2005 | Allen et al. |
| 2010/0324124 | A1 | 12/2010 | Irvine et al. |
| 2013/0053470 | A1 | 2/2013 | Raisin-Dadre et al. |
| 2013/0216607 | A1 * | 8/2013 | Szoka, Jr. ............ C07J 41/0055 552/544 |
| 2015/0004218 | A1 | 1/2015 | Balu-Iyer |
| 2017/0219467 | A1 | 8/2017 | Henry et al. |

FOREIGN PATENT DOCUMENTS

| | | | |
|---|---|---|---|
| CN | 103917548 A | 7/2014 | |
| EP | 3 058 953 A1 | 8/2016 | |
| JP | 11-193247 A | 7/1999 | |
| JP | 2015-96567 A | 5/2015 | |
| WO | 94/28939 A1 | 12/1994 | |
| WO | 2011/057224 A2 | 5/2011 | |
| WO | WO-2012175923 A1 * | 12/2012 | ............. A61L 27/34 |
| WO | 2013/155493 A1 | 10/2013 | |
| WO | 2016/036902 A1 | 3/2016 | |
| WO | 2017/003639 A2 | 1/2017 | |

OTHER PUBLICATIONS

Office Action mailed Sep. 5, 2022, issued in related Chinese Application No. 201980033942.0, filed Mar. 25, 2019, 15 pages.
Asghari, F., et al., "Biodegradable and Biocompatible Polymers for Tissue Engineering Application: a Review," Artificial Cells, Nanomedicine, and Biotechnology, 45(2):185-192, 2017.
Birge, R.B., et al., "Phosphatidylserine Is a Global Immunosuppressive Signal in Efferocytosis, Infectious Disease, and Cancer," Cell Death and Differentiation 23:962-978, Feb. 2016.
Bosetti, M, et al., "Effects of Phosphatidylserine Coatings on Titanium on Inflammatory Cells and Cell-Induced Mineralisation in vitro," Biomaterials 26(36):7572-7578, Dec. 2005.
Comfurius, P., et al., "The Enzymatic Synthesis of Phosphatidylserine and Purification by CM-Cellulose Column Chromatography," Biochimica et Biophysica Acta (BBA)—Lipids and Lipid Metabolism 488(1):36-42, Jul. 1977.
Cong, X., et al., "Unquenchable Surface Potential Dramatically Enhances Cu2+ Binding to Phosphatidylserine Lipids," Journal of the American Chemical Society 137(24):7785-7792, Jun. 2015.
Hotaling, N., et al., "Biomaterial Strategies for Immunomodulation," Annual Review of Biomedical Engineering 17:317-349, 2015.
International Search Report and Written Opinion dated May 23, 2019, issued in PCT/US2019/023921, filed Mar. 25, 2019, 14 pages.
Kim, H., et al., "Synthesis of Biomembrane-Mimic Polymers With Various Phospholipid Head Groups," Polymer 55:517-524, 2014.
Kurosaki, T., et al., "Splenic Gene Delivery System Using Self-Assembling Nano-Complex With Phosphatidylserine Analog," Biological and Pharmaceutical Bulletin 38(1):23-29, 2015.
Liu, S., et al., "Chemical Conjugation of Zwitterionic Polymers Protects Immunogenic Enzyme and Preserves Bioactivity Without Polymer-Specific Antibody Response," NanoToday 11(3):285-291, 2016.
Maitz, M.F., "Applications of Synthetic Polymers in Clinical Medicine," Biosurface and Biotribology, 1:161-176, 2015.
Nakagawa, Y., et al., "Apoptotic Cell Membrane-Inspired Polymer for Immunosuppression" ACS Macro Letters 6(9):1020-1024, 2017.

(Continued)

*Primary Examiner* — Stacy B Chen
(74) *Attorney, Agent, or Firm* — Christensen O'Connor Johnson Kindness PLLC

(57) ABSTRACT

Zwitterionic phosphatidylserine (ZPS) monomers, ZPS polymers and ZPS copolymers, methods for making the ZPS monomers, ZPS polymers, and ZPS copolymers, compositions and materials that include ZPS polymers and ZPS copolymers, and methods for using the ZPS monomers, ZPS polymers, and ZPS copolymers.

14 Claims, 8 Drawing Sheets

(56) References Cited

OTHER PUBLICATIONS

Nakagawa, Y., et al., "Rational Design of Anti-Inflammatory Polymers Inspired by Apoptotic Cell Death Using Phosphoramidite Chemistry," Polymer 134:85-93, Jan. 2018.

Punnamaraju, S., et al., "Triggered Release of Molecules Across Droplet Interface Bilayer Lipid Membranes Using Photopolymerizable Lipids," Langmuir 28(20):7657-7664, May 2012.

Roberts, R., et al., "Towards Programming Immune Tolerance Through Geometric Manipulation of Phosphatidylserine," Biomaterials 72:1-10, Dec. 2015.

Ulery, B., et al., "Biomedical Applications of Biodegradable Polymers," Journal of Polymer Science Part B: Polymer Physics 49(12):832-864, 2011.

Extended European Search Report mailed Dec. 7, 2021, issued in related European Patent Application No. 19775204, filed Mar. 25, 2019, 9 pages.

Lampkins, A.J., et al., "Bio-orthogonal Phosphatidylserine Conjugates for Delivery and Imaging Applications," Journal of Organic Chemistry 73(16):6053-6058, Aug. 1, 2008.

\* cited by examiner

IMMUNOSUPPRESSIVE MATERIALS AND RELATED METHODS

CROSS-REFERENCE TO RELATED APPLICATION

This application is a National Stage of International Application No. PCT/US2019/023921 filed Mar. 25, 2019, which claims the benefit of U.S. Application No. 62/647,534, filed Mar. 23, 2018, the disclosure of each of which is expressly incorporated herein by reference in its entirety.

STATEMENT OF GOVERNMENT LICENSE RIGHTS

This invention was made with government support under Grant No. HDTRA1-13-1-0044 awarded by the Defense Threat Reduction Agency and Grant No. DMR-1708436 awarded by the National Science Foundation. The government has certain rights in the invention.

BACKGROUND OF THE INVENTION

When considering a biomaterial for in vivo applications, the first and most important requirement is biocompatibility with the human body. In addition to inert biomaterials, functional biomaterials that can actively control and modulate immune responses are another approach. It is found that apoptotic cells can direct immune cells such as macrophages and dendritic cells to immunosuppressive phenotypes via externalized phosphatidylserine (PS) on their surface and thus induce immune tolerance even in inflammatory activated regions.

A need exists to develop improved nonfouling polymers and compositions and materials that include these polymers having advantageous nonfouling properties. The present invention seeks to fulfill this need and provides further related advantages.

SUMMARY OF THE INVENTION

The present invention provides zwitterionic phosphatidylserine (ZPS) monomers, ZPS polymers and ZPS copolymers, methods for making the ZPS monomers, ZPS polymers, and ZPS copolymers, compositions and materials that include ZPS polymers and ZPS copolymers, and methods for using the ZPS monomers, ZPS polymers, and ZPS copolymers.

The present invention also provides non-zwitterionic (neutral) phosphatidylserine (NZPS) monomers, polymers, copolymers, compositions and materials that include the same, and methods for making and using the same.

In one aspect, the invention provides particles that include one or more zwitterionic phosphatidylserine polymers in which the polymer is coupled to the particle. In one embodiment, the particle has micro- or nanoscale dimensions and comprises one or more zwitterionic phosphatidylserine polymers coupled to the particle. In certain embodiments, the polymer is covalently coupled to the particle. In other embodiments, the polymer is physically adsorbed to the particle. As used herein, the term "microscale dimensions" refers to a particle having a diameter of about 1 µm or greater. As used herein, the term "nanoscale dimensions" refers to a particle having a diameter less than 1 µm.

In certain embodiments, the particle is a biomolecule and the biomolecule modified to include the polymer is a bioconjugate. Representative biomolecules useful in the invention include proteins, nucleic acids, glycoproteins, lipids, and proteoglycans. Representative proteins that include enzymes, signaling proteins (e.g., a hormone, a cytokine, a regulatory protein, an insulin, a PD-1/PD-L1/2 inhibitor), haemostasis or thrombosis proteins, vaccines, complement system proteins, and antibodies or functional fragments or characteristic portions thereof. In certain embodiments, the biomolecule is a biomolecule that has been previously modified, such as a PEGylated biomolecule (e.g., a protein that has been modified to include one or more poly(ethylene glycol)s.

In other embodiments, the biomolecule is a small molecule therapeutic agent (a carbon-based therapeutic agent having a molecular weight less than about 1000 g/mole, preferably less than about 800 g/mole).

In further embodiments, the particle is a drug delivery vehicle. Representative drug delivery vehicles include micelles, liposomes, and polymersomes (e.g., containing one or more therapeutic and/or diagnostic agents).

In certain embodiments, the particle is a cell, a virus, or a bacterium.

In other embodiments, the particle is a hydrogel, such as a microgel or a nanogel.

In further embodiments, the particle is a metal, a metal oxide, a ceramic, a synthetic polymer, a natural polymer, a crystal, a semiconductor material, a grapheme, a graphene oxide, an iron oxide, or a silica, or a quantum dot.

In certain embodiments, the particles have one or more zwitterionic phosphatidylserine polymers grafted from the particle. In other embodiments, the particles have one or more zwitterionic phosphatidylserine polymers grafted to the particle.

In certain embodiments, the particle includes one or more zwitterionic phosphatidylserine polymers that have repeating units having the formula:

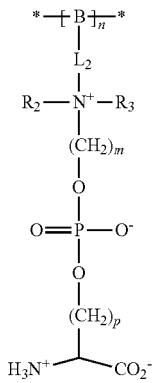

wherein
* indicates the point of attachment of the repeating unit to other repeating units in the polymer or copolymer, or polymer or copolymer terminal groups;
B is a polymer backbone;
$L_2$ is a linker group selected from $-(CH_2)_x-$, $-C(=O)NH(CH_2)_x-$, $-C(=O)O(CH_2)_x-$, $-C(=O)OC(=O)O(CH_2)_x-$, $-(CH_2)_x-O-(CH_2)_x-$, and $-(CH_2)_x-S-S-(CH_2)_x-$, where x at each occurrence is an integer independently selected from 1 to 20;
$R_2$ and $R_3$ are independently selected from the group consisting of hydrogen, $C_1$-$C_{20}$ alkyl, and $C_6$-$C_{12}$ aryl;
m is an integer from 1 to 20;
p is an integer from 1 to 20; and
n is an integer from about 10 to about 500.

In other embodiments, the particle includes one or more zwitterionic phosphatidylserine polymers that have repeating units having the formula:

$$*\left[R_4-L_3-\underset{\underset{L_2}{|}}{\overset{\overset{R_1}{|}}{L}}-L_4-R_5\right]_n*$$

$$R_2-N^+-R_3$$
$$|$$
$$(CH_2)_m$$
$$|$$
$$O$$
$$|$$
$$O=P-O^-$$
$$|$$
$$O$$
$$|$$
$$(CH_2)_p$$
$$H_3N^+\diagdown CO_2^-$$

wherein
* indicates the point of attachment of the repeating unit to other repeating units in the polymer or copolymer, or polymer or copolymer terminal groups;

$R_1$ is selected from the group consisting of hydrogen, fluorine, trifluoromethyl, cyano, $C_1$-$C_{20}$ alkyl, and $C_6$-$C_{12}$ aryl $R_2$ and $R_3$ are independently selected from the group consisting of hydrogen, $C_1$-$C_{20}$ alkyl, and $C_6$-$C_{12}$ aryl, or $R_2$ and $R_3$ taken together with the nitrogen form a ring;

$R_4$ and $R_5$ are the residues of polymerization of polymerizable functional groups;

L is C or Si;

$L_2$ is a linker group selected from —$(CH_2)_x$—, —C(=O)NH$(CH_2)_x$—, —C(=O)O$(CH_2)_x$—, —C(=O)OC(=O)O$(CH_2)_x$—, —$(CH_2)_x$—O—$(CH_2)_x$—, and —$(CH_2)_x$—S—S—$(CH_2)_x$—, where x at each occurrence is an integer independently selected from 1 to 20;

$L_3$ and $L_4$ are independently selected from —$(CH_2)_x$—, —C(=O)NH$(CH_2)_x$—, —C(=O)O$(CH_2)_x$—, —C(=O)OC(=O)O$(CH_2)_x$—, —$(CH_2)_x$—O—$(CH_2)_x$—, and —$(CH_2)_x$—S—S—$(CH_2)_x$—, where x at each occurrence is an integer independently selected from 0 to 20;

m is an integer from 1 to 20;

p is an integer from 1 to 20; and n is an integer from about 10 to about 500.

In further embodiments, the particle includes one or more zwitterionic phosphatidylserine polymers that have repeating units having the formula:

$$*\left(\underset{\underset{}{}}{CH_2}-\underset{\underset{}{\overset{|}{\underset{}{}}}}{\overset{R_1}{\underset{|}{C}}}\right)_a*$$
$$\|$$
$$O$$
$$|$$
$$X$$
$$|$$
$$(CH_2)_n$$
$$|$$
$$R_2-N^+-R_3$$
$$|$$
$$(CH_2)_m$$
$$|$$
$$O$$
$$|$$
$$O=P-O^-$$
$$|$$
$$O$$
$$|$$
$$(CH_2)_p$$
$$H_3N^+\diagdown CO_2^-$$

wherein
* indicates the point of attachment of the repeating unit to other repeating units in the polymer or copolymer, or polymer or copolymer terminal groups;

$R_1$ is selected from the group consisting of hydrogen, fluorine, trifluoromethyl, cyano, $C_1$-$C_{20}$ alkyl, and $C_6$-$C_{12}$ aryl;

$R_2$ and $R_3$ are independently selected from hydrogen and $C_1$-$C_6$ alkyl, or $R_2$ and $R_3$ taken together with the nitrogen form a ring;

X is O or NH, n is an integer from 1 to 20;

m is an integer from 1 to 20;

p is an integer from 1 to 20; and a is an integer from about 10 to about 500.

In another aspect, the invention provides methods for rendering a particle immunosuppressive. In one embodiment, the methods comprise covalently coupling one or more zwitterionic phosphatidylserine polymers to the particle.

In another aspect, the invention provides substrate surfaces having one or more zwitterionic phosphatidylserine polymers covalently coupled thereto.

In other aspects, the invention also provides particles having micro- or nanoscale dimensions comprising one or more neutral (non-zwitterionic) phosphatidylserine polymers covalently coupled to a particle, methods for rendering a particle immunosuppressive comprising covalently coupling one or more neutral (non-zwitterionic) phosphatidylserine polymers to a particle, and substrate surfaces having one or more neutral (non-zwitterionic) phosphatidylserine polymers covalently coupled thereto.

In a further aspect, the invention provides ZPS monomers. In these embodiments, the monomer comprises a polymerizable moiety covalently coupled to a zwitterionic phosphatidylserine moiety.

In one embodiment, the ZPS monomer has the formula:

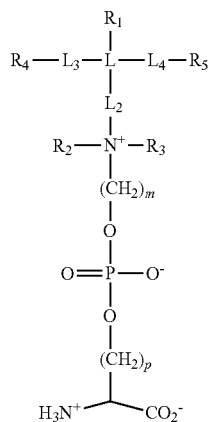

wherein
- $R_1$ is selected from the group consisting of hydrogen, fluorine, trifluoromethyl, cyano, $C_1$-$C_{20}$ alkyl, and $C_6$-$C_{12}$ aryl;
- $R_2$ and $R_3$ are independently selected from the group consisting of hydrogen, $C_1$-$C_{20}$ alkyl, and $C_6$-$C_{12}$ aryl, or $R_2$ and $R_3$ taken together with the nitrogen form a ring;
- $R_4$ and $R_5$ are independently selected from functional groups suitable for polymerization by addition, condensation or free radical polymerization;
- L is C or Si;
- $L_2$ is independently selected from $-(CH_2)_x-$, $-C(=O)NH(CH_2)_x-$, $-C(=O)O(CH_2)_x-$, where x is an integer from 1 to 20;
- $L_3$ and $L_4$ are independently selected from $-(CH_2)_x-$, $-C(=O)NH(CH_2)_x-$, $-C(=O)O(CH_2)_x-$, $-C(=O)OC(=O)O(CH_2)_x-$, $-(CH_2)_x-O-(CH_2)_x-$, and $-(CH_2)_x-S-S-(CH_2)_x-$, where x at each occurrence is an integer independently selected from 0 to 20;
- m is an integer from 1 to 20; and
- p is an integer from 1 to 20.

In another embodiment, the ZPS monomer has the formula:

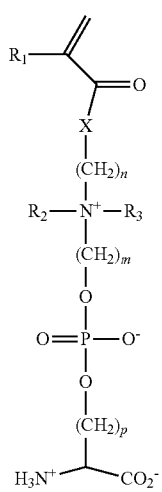

wherein,
- $R_1$ is selected from the group consisting of hydrogen, fluorine, trifluoromethyl, cyano, $C_1$-$C_{20}$ alkyl, and $C_6$-$C_{12}$ aryl,
- $R_2$ and $R_3$ are independently selected from hydrogen and $C_1$-$C_6$ alkyl, or $R_2$ and $R_3$ taken together with the nitrogen form a ring,
- X is O or NH,
- n is an integer from 1 to 20,
- m is an integer from 1 to 20, and
- p is an integer from 1 to 20.

In another aspect, the invention provides ZPS polymers and copolymers. In these embodiments, the ZPS polymer or copolymer has repeating units, wherein one or more repeating units comprise a zwitterionic phosphatidylserine moiety. In certain embodiments, the zwitterionic phospatidylserine moiety is pendant from the polymer backbone. In other embodiments, the zwitterionic phospatidylserine moiety is a component of the polymer backbone (e.g., part of the zwitterionic phospatidylserine moiety is in the polymer backbone).

In certain embodiments, the ZPS polymer or copolymer includes repeating units having the formula:

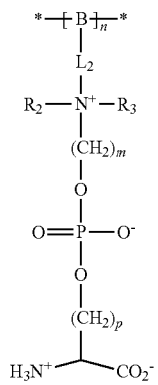

wherein
- \* indicates the point of attachment of the repeating unit to other repeating units in the polymer or copolymer, or polymer or copolymer terminal groups;
- B is a polymer backbone;
- $L_2$ is a linker group that links the ZPS moiety to the backbone, representative groups include $-(CH_2)_x-$, $-C(=O)NH(CH_2)_x-$, $-C(=O)O(CH_2)_x-$, $-C(=O)OC(=O)O(CH_2)_x-$, $-(CH_2)_x-O-(CH_2)_x-$, and $-(CH_2)_x-S-S-(CH_2)_x-$, where x at each occurrence is an integer independently selected from 1 to 20;
- $R_2$ and $R_3$ are independently selected from the group consisting of hydrogen, $C_1$-$C_{20}$ alkyl, and $C_6$-$C_{12}$ aryl, or $R_2$ and $R_3$ taken together with the nitrogen form a ring;
- m is an integer from 1 to 20;
- p is an integer from 1 to 20; and
- n is an integer from about 10 to about 500.

In other embodiments, the ZPS polymer or copolymer includes repeating units having the formula:

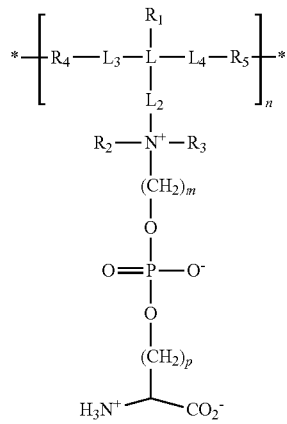

wherein
* indicates the point of attachment of the repeating unit to other repeating units in the polymer or copolymer, or the polymer or copolymer terminal groups;
$R_1$ is selected from the group consisting of hydrogen, fluorine, trifluoromethyl, cyano, $C_1$-$C_{20}$ alkyl, and $C_6$-$C_{12}$ aryl;
$R_2$ and $R_3$ are independently selected from the group consisting of hydrogen, $C_1$-$C_{20}$ alkyl, and $C_6$-$C_{12}$ aryl, or $R_2$ and $R_3$ taken together with the nitrogen form a ring;
$R_4$ and $R_5$ are independently selected from residues of polymerization of the functional groups suitable for polymerization by addition, condensation or free radical polymerization;
L is C or Si;
$L_2$ is independently selected from —$(CH_2)_x$—, —C(=O)NH$(CH_2)_x$—, —C(=O)O$(CH_2)_x$—, where x is an integer from 1 to 20;
$L_3$ and $L_4$ are independently selected from —$(CH_2)_x$—, —C(=O)NH$(CH_2)_x$—, —C(=O)O$(CH_2)_x$—, —C(=O)OC(=O)O$(CH_2)_x$—, —$(CH_2)_x$—O—$(CH_2)_x$—, and —$(CH_2)_x$—S—S—$(CH_2)_x$—, where x at each occurrence is an integer independently selected from 0 to 20;
m is an integer from 1 to 20;
p is an integer from 1 to 20; and
n is an integer from about 10 to about 500.

In further embodiments, the ZPS polymer or copolymer includes repeating units having the formula:

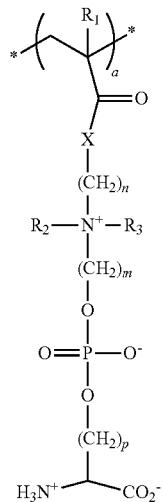

wherein
* indicates the point of attachment of the repeating unit to other repeating units in the polymer or copolymer, or the polymer or copolymer terminal groups;
$R_1$ is selected from the group consisting of hydrogen, fluorine, trifluoromethyl, cyano, $C_1$-$C_{20}$ alkyl, and $C_6$-$C_{12}$ aryl;
$R_2$ and $R_3$ are independently selected from hydrogen and $C_1$-$C_6$ alkyl, or $R_2$ and $R_3$ taken together with the nitrogen form a ring;
X is O or NH;
n is an integer from 1 to 20;
m is an integer from 1 to 20;
p is an integer from 1 to 20; and
a is an integer from about 10 to about 500.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

µg/ml) for 18 hours followed by the stimulation of LPS (100 ng/mL) for 48 h, where the nanogel solutions were pre-incubated with Annexin V solution at various concentrations (0, 10, 25, 50, 100, 200 µg/ml) for 6 h, as measured by ELISA.

Figure 2A:
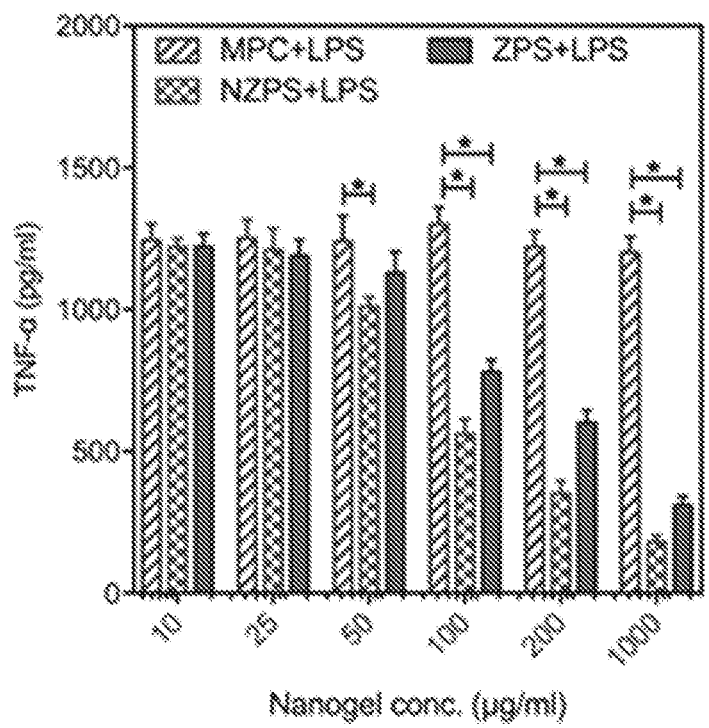
FIG. 2A compares the level of TNF-α secretion in the supernatant from RAW 264.7 macrophages ($10^5$/well) treated with MPC, NZPS, or ZPS nanogel solutions at various concentration (10, 25, 50, 100, 200, 1000 μg/ml) for 18 hours followed by the stimulation of LPS (100 ng/mL) for 48 h, as measured by ELISA.
Figure 2B:
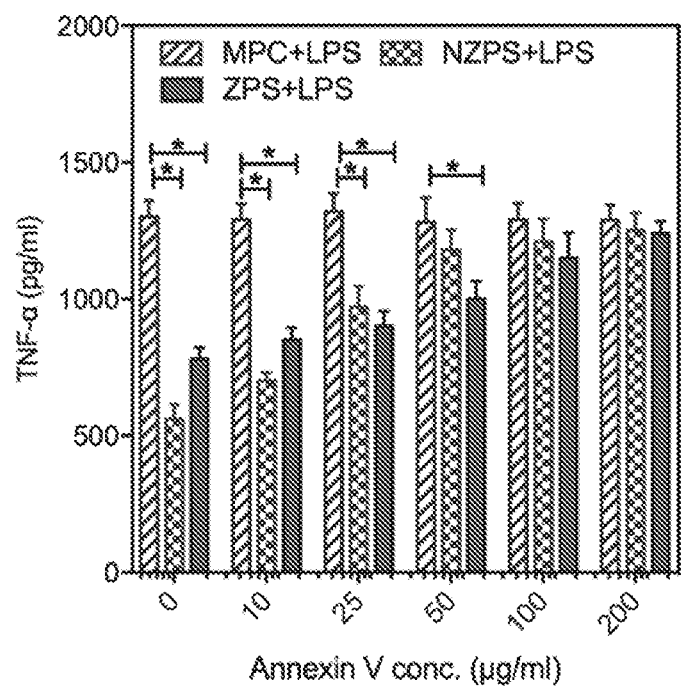
FIG. 2B compares the level of TNF-α secretion in the supernatant from RAW 264.7 macrophages ($10^5$/well) treated with MPC, NZPS, or ZPS nanogel solutions at 100
Figure 2C:
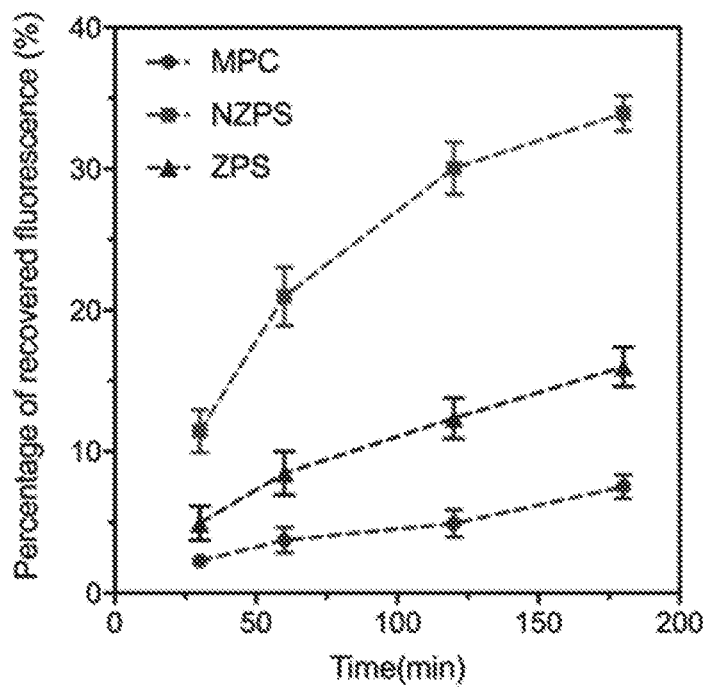

FIG. 2C compares recovered fluorescence from RAW 264.7 macrophages ($10^5$/well) incubated with MPC, NZPS, and ZPS nanogels encapsulating FITC-BSA for 30, 60, 120, and 180 min, after which the cells were washed and lysed for the detection of recovered fluorescence.

Figure 3A:
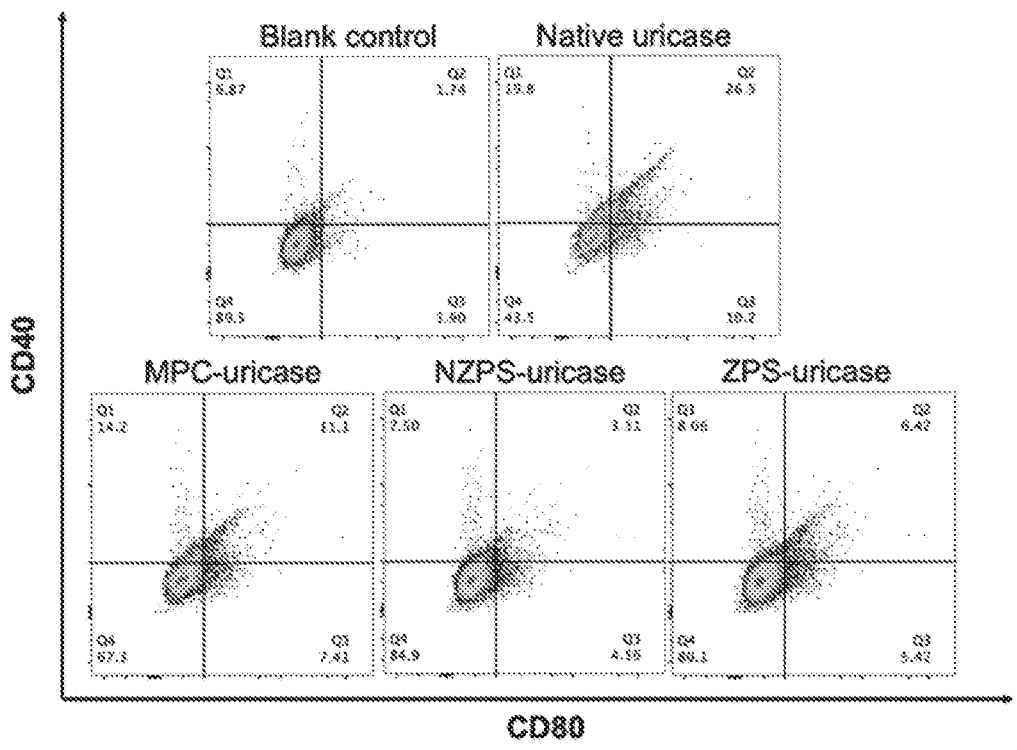

FIG. 3A compares CD40/CD80 for DC 2.4 dendritic cells incubated with native uricase, MPC-uricase, NZPS-uricase, and ZPS-uricase conjugates for 72 hours relative to blank control and stained for flow cytometry.

(B) Summary of the percentage of dendritic cells that maintained an immature status (CD40– CD80–). (C) The secretion of TGF-beta into the supernatant was detected by ELISA kit.

Figure 3B:
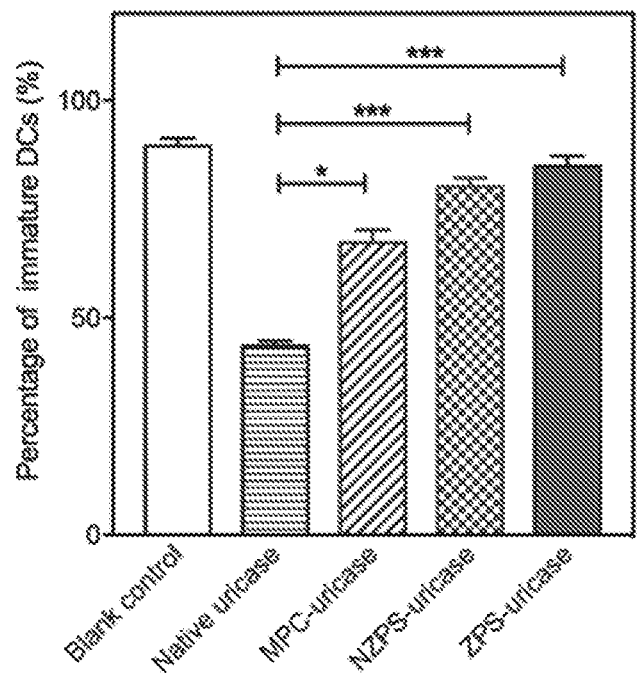

FIG. 3B compares percentage of dendritic cells that maintained an immature status (CD40– CD80–) for the dendritic cells described in FIG. 3A.

Figure 3C:
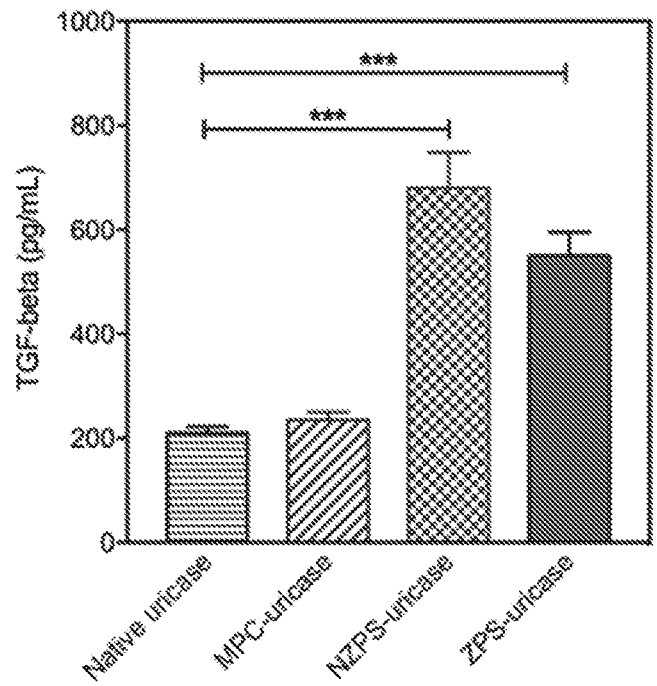

FIG. 3C compares TGF-beta secretion for the dendritic cells described in FIG. 3A, as measured by ELISA.

Figure 4A:
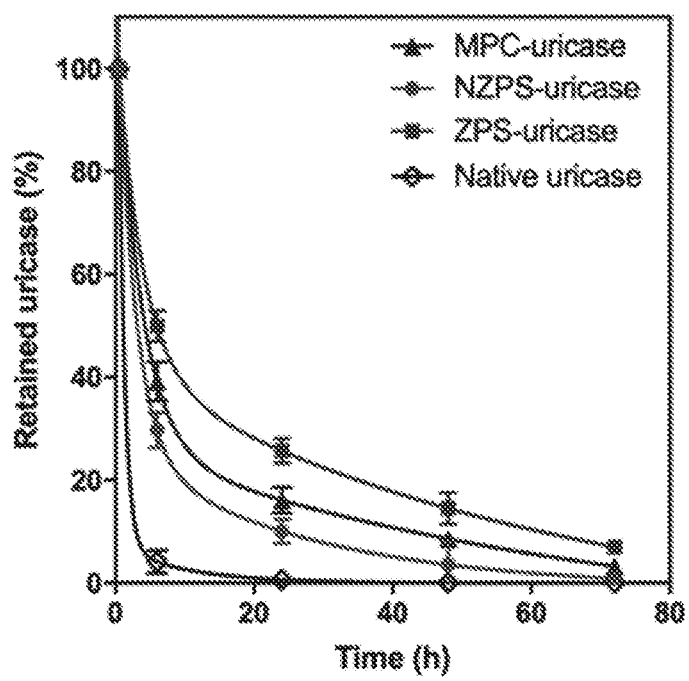
Figure 4B:
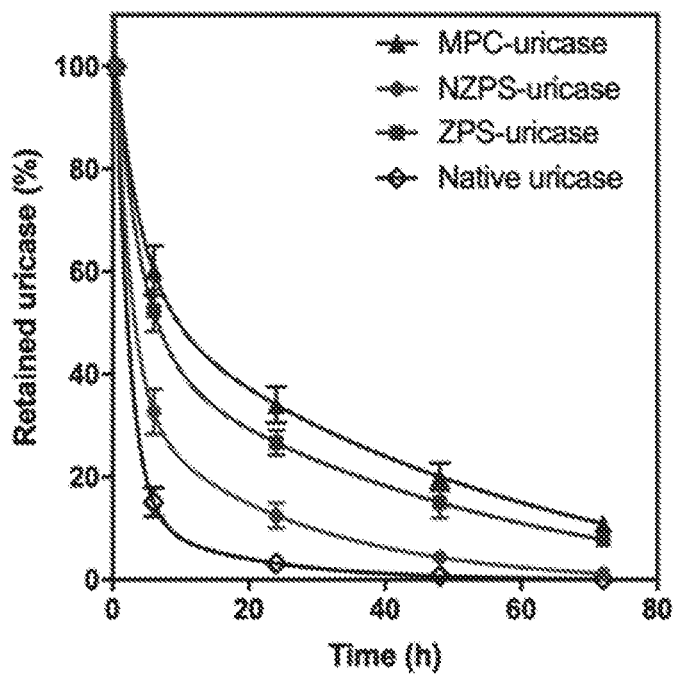

FIGS. 4A and 4B compare circulation time of native uricase, ZPS-uricase, NZPS-uricase, MPC-uricase conjugates after the first (4A) and third (4B) injection in mice.

Figure 4C:
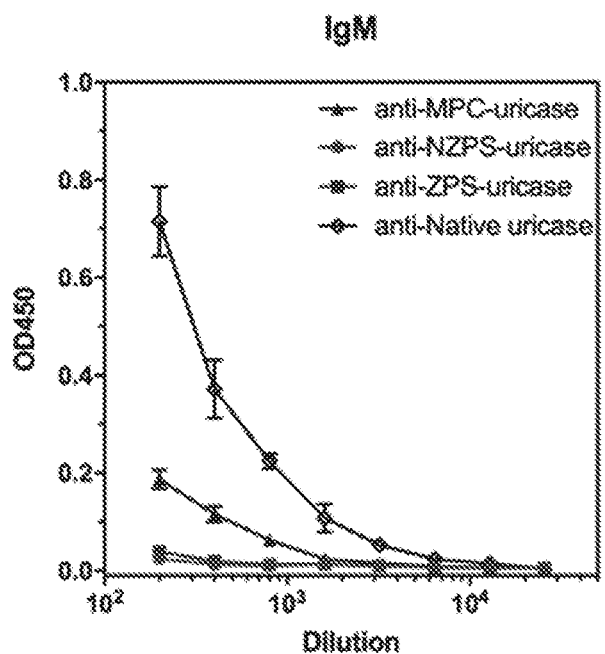
Figure 4D:
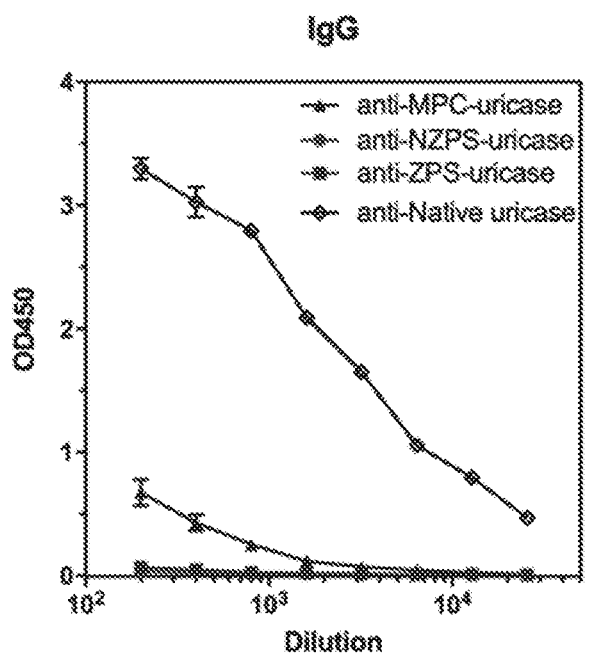

FIGS. 4C and 4D compare detection of IgM (4C) and IgG (4D) specific to uricase or uricase conjugates. Mice were sacrificed on 21st day and their sera were harvested for the detection of IgM and IgG specific to uricase or uricase conjugates via ELISA test.

Figure 4E:
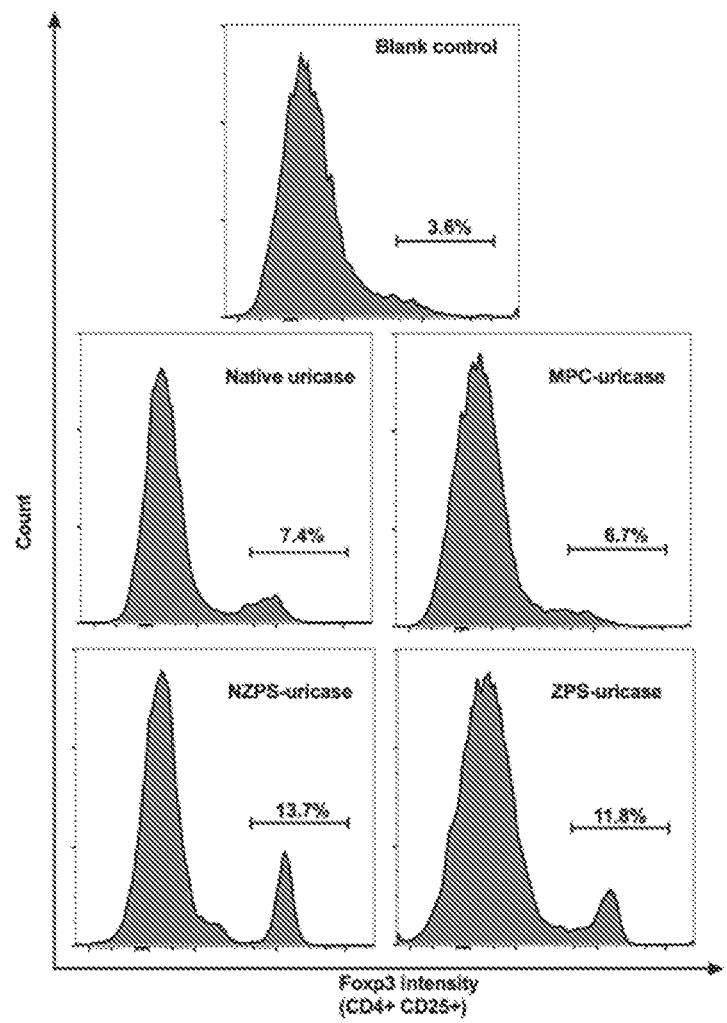

FIG. 4E compares Treg phenotype (Foxp3+) cells among CD4+CD25+ splenocytes for mice treated with native uricase, ZPS-uricase, NZPS-uricase, and MPC-uricase conjugates for 72 hours and then stained for flow cytometry, relative to blank control. Summary of the percentage of Treg phenotype (Foxp3+) cells among CD4+CD25+ splenocytes.

Figure 4F:
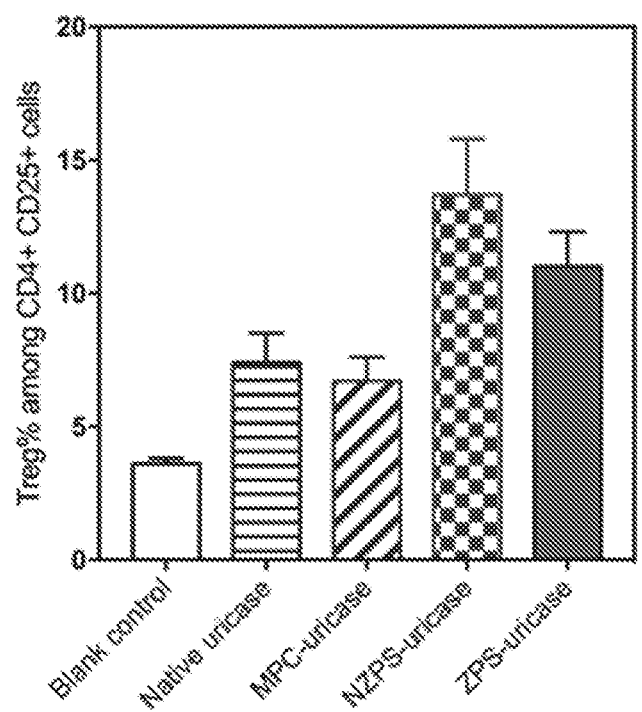

FIG. 4F compares Treg % among CD4+CD25+ cells for mice treated as described in FIG. 4E.

DETAILED DESCRIPTION OF THE INVENTION

In one aspect, the present invention provides zwitterionic phosphatidylserine (ZPS) monomers, ZPS polymers and ZPS copolymers, methods for making the ZPS monomers, ZPS polymers, and ZPS copolymers, compositions and materials that include ZPS polymers and ZPS copolymers, and methods for using the ZPS monomers, ZPS polymers, and ZPS copolymers.

As used herein, the term "zwitterionic phosphatidylserine monomer" or "ZPS monomer" refers to a polymerizable monomer or a pendant group of a homopolymer or copolymer that includes a phosphatidylserine moiety ($NH_2$—CH(—$CH_2O$—P(=O)($O^-$))—$CO_2H$ and its ionic forms) and an additional cationic center (e.g., —$N^+(R^a)(R^b)$—, where $R^a$ and $R^b$ are independently H or $C_1$-$C_3$ alkyl). The monomer or pendant group of the homopolymer or copolymer is zwitterionic by virtue of the cationic N center and the anionic phosphate center.

A representative ZPS monomer has formula (I):

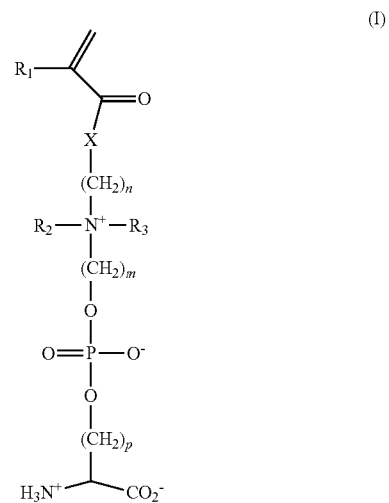

wherein, in certain embodiments, $R_1$ is selected from the group consisting of hydrogen, fluorine, trifluoromethyl, cyano, $C_1$-$C_{20}$ alkyl (preferably $C_1$-$C_6$ alkyl), and $C_6$-$C_{12}$ aryl, $R_2$ and $R_3$ are independently selected from hydrogen and $C_1$-$C_6$ alkyl, or $R_2$ and $R_3$ taken together with the nitrogen form a ring, X is O or NH, n is an integer from 1 to 20 (e.g., 1, 2, 3, 4, 5, or 6), m is an integer from 1 to 20 (e.g., 1, 2, 3, 4, 5, or 6), and p is an integer from 1 to 20 (e.g., 1, 2, 3, 4, 5, or 6).

The term "zwitterionic phosphatidylserine polymer" or "ZPS polymer" refers to a polymer (i.e., homopolymer or copolymer) having one or more pendant groups that include a phosphatidylserine moiety and an additional cationic center, as described above. The polymer is zwitterionic by virtue of the cationic N center and the anionic phosphate center in the repeating unit pendant group.

A ZPS homopolymer polymer is prepared by polymerization of a monomer of formula (I) and a ZPS copolymer is prepared by copolymerization a monomer of formula (I) and a comonomer. These ZPS polymers (homopolymers, random copolymers, block copolymers) include repeating units having pendant zwitterionic phosphatidylserine (ZPS) moieties, as shown below:

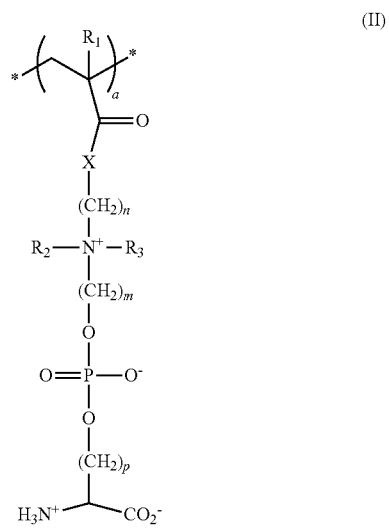

wherein, in certain embodiments, $R_1$, $R_2$, $R_3$, X, n, m, and p are as described above for the monomer of formula (I), a is an integer from about 10 to about 500, and * indicates the point of attachment of the repeating unit to other repeating units in the polymer or copolymer, or the polymer or copolymer terminal groups.

As described herein, the ZPS monomers can be readily polymerized under standard polymerizing conditions to provide ZPS polymers.

ZPS Monomers, ZPS Polymers, and ZPS Copolymers

In certain aspects, the present invention provides ZPS monomers and ZPS polymers and ZPS copolymers prepared from ZPS monomers.

Monomers of the invention include (a) ZPS monomers with backbones selected from silicone, fluorinated, peptide, urethane, urea, imide, carbonate, anhydride, phosphazene, epoxy, sulfone, and sulfide backbones, and degradable backbones beyond methacrylate and acrylate backbones, (b) linear ZPS crosslinkers, degradable and non-degradable ZPS-based crosslinkers, or (c) linear ZPS-based monomers that provide ZPS groups in the polymer backbone or ZPS groups in the polymer side chains.

Polymers and copolymers of the invention include polymers and copolymers, such as homopolymers, random copolymers, block copolymers, multiblock copolymers, and branched or star polymers that include repeating units containing ZPS groups, including such polymers prepared from polymerization (or copolymerization) of one or more monomers of the invention (e.g., ZPS monomers).

ZPS monomers. In one aspect, the invention provides ZPS monomers. The ZPS monomers provide ZPS polymers and ZPS copolymers that include ZPS-containing repeating units. The ZPS groups of the repeating units and polymers may be pendant ZPS groups (i.e., polymer side chains).

In certain embodiments, the ZPS monomer comprises a polymerizable moiety covalently coupled to a zwitterionic phosphatidylserine moiety.

In certain embodiments, ZPS monomers include monomers that provide polymers or copolymers having pendant ZPS groups (polymer side chains). Representative ZPS monomers have formula (I) shown above. Other representative ZPS monomers have formula (III):

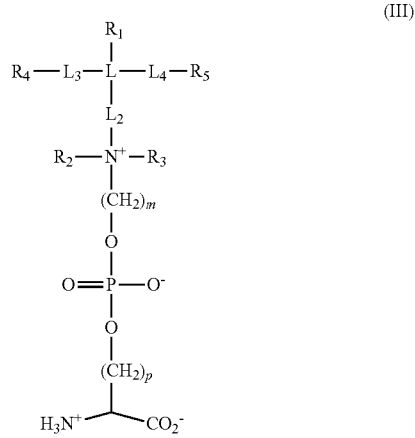

(III)

wherein
$R_1$ is selected from the group consisting of hydrogen, fluorine, trifluoromethyl, cyano, $C_1$-$C_{20}$ alkyl, and $C_6$-$C_{12}$ aryl;

$R_2$ and $R_3$ are independently selected from the group consisting of hydrogen, $C_1$-$C_{20}$ alkyl (e.g., $C_1$-$C_3$ alkyl), and $C_6$-$C_{12}$ aryl, or $R_2$ and $R_3$ taken together with the nitrogen form a ring;

$R_4$ and $R_5$ are independently selected from functional groups suitable for polymerization by addition, condensation or free radical polymerization;

L is C or Si;

$L_2$ is independently selected from $-(CH_2)_x-$, $-C(=O)NH(CH_2)_x-$, $-C(=O)O(CH_2)_x-$, where x is an integer from 1 to 20 (e.g., 1, 2, 3, 4, 5, or 6);

$L_3$ and $L_4$ are independently selected from $-(CH_2)_x-$, $-C(=O)NH(CH_2)_x-$, $-C(=O)O(CH_2)_x-$, $-C(=O)OC(=O)O(CH_2)_x-$, $-(CH_2)_x-O-(CH_2)_x-$, and $-(CH_2)_x-S-S-(CH_2)_x-$, where x at each occurrence is an integer independently selected from 0 to 20, preferably from 1 to 20 (in certain embodiments, $L_3$ and/or $L_4$ is absent);

m is an integer from 1 to 20 (e.g., 1, 2, 3, 4, 5, or 6); and p is an integer from 1 to 20 (e.g., 1, 2, 3, 4, 5, or 6).

The preparation of a representative ZPS monomer useful for making the polymers and copolymers of the invention is described in Example 1.

It will be appreciated that the ZPS polymers and copolymers of the invention used for making the inventive surface coatings, bulk materials, standalone materials, hydrogels, and conjugates can be prepared from the monomers described herein, including the methacrylate/methacrylamide ZPS monomer of formula (I) and the ZPS monomer of formula (III).

ZPS polymers and copolymers. In other aspects, the invention provides ZPS polymers prepared from ZPS monomers, as described herein, and that include ZPS repeating units.

In certain embodiments, the ZPS polymer or copolymer has repeating units, wherein one or more repeating units include a zwitterionic phosphatidylserine moiety. In certain of these embodiments, the zwitterionic phospatidylserine moiety is pendant from the polymer backbone. In other of these embodiments, the zwitterionic phospatidylserine moiety is a component of the polymer backbone (e.g., part of the zwitterionic phospatidylserine moiety is in the polymer backbone).

In certain embodiments for these polymers and copolymers, the polymer and copolymer backbone can be any one of a polyester, a polypeptide, a polyimide, a polyphosphazene, a polysiloxane, a polyepoxy, a vinyl polymer, a phenolic polymer, a polyurethane, a polyurea, a polycarbonate, a polysulfone, or a polysulfide.

The ZPS polymers and copolymers of the invention include polymers and copolymers prepared from monomers of formulae (I) and (III). Polymers can be formed by polymerization of (a) a monomer of formula (I), (b) a monomer of formula (III), or (c) a comonomers of formulae (I) and (III). Copolymers can be prepared by copolymerization of (a) a monomer of formula (I) and a second comonomer that is suitable for copolymerization with a monomer of formula (I), (b) a monomer of formula (III) and a second comonomer that is suitable for copolymerization with a monomer of formula (I), and (c) a monomer of formula (I) and a monomer of formula (III) that is suitable for copolymerization with a monomer of formula (I).

In certain embodiments, the ZPS monomer provides a polymer repeating unit that includes an ZPS moiety that is pendant from the polymer backbone (i.e., forms a part of the polymer side chain). Representative polymers having ZPS moieties that are pendant from the polymer backbone have formula (II) shown above. Other representative ZPS polymers have formula (IV):

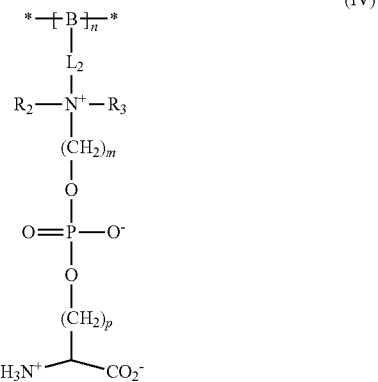

(IV)

wherein
* indicates the point of attachment of the repeating unit to other repeating units in the polymer or copolymer, or polymer or copolymer terminal groups;
B is a polymer backbone as described above;
$L_2$ is a linker group that links the ZPS moiety to the backbone, representative groups include —$(CH_2)_x$—, —C(=O)NH$(CH_2)_x$—, —C(=O)O$(CH_2)_x$—, —C(=O)OC(=O)O$(CH_2)_x$—, —$(CH_2)_x$—O—$(CH_2)_x$—, and —$(CH_2)_x$—S—S—$(CH_2)_x$—, where x at each occurrence is an integer independently selected from 1 to 20;
$R_2$ and $R_3$ are independently selected from the group consisting of hydrogen, $C_1$-$C_{20}$ alkyl (e.g., $C_1$-$C_3$ alkyl, and including cyclic alkyl, such as $C_3$-$C_7$ cycloalkyl), and $C_6$-$C_{12}$ aryl, or $R_2$ and $R_3$ taken together with the nitrogen form a ring;
m is an integer from 1 to 20 (e.g., 1, 2, 3, 4, 5, or 6);
p is an integer from 1 to 20 (e.g., 1, 2, 3, 4, 5, or 6); and
n is an integer from about 10 to about 500.

In other embodiments, representative polymers having ZPS moieties that are pendant from the polymer backbone have formula (V):

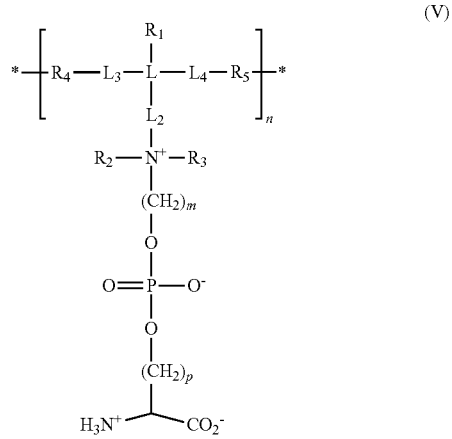

(V)

wherein $R_1$, $R_2$, $R_3$, $R_4$, $R_5$, L, $L_2$, $L_3$, $L_4$, m, p, and * are as described above for the monomer of formula (II), with the understanding that $R_4$ and $R_5$ in formula (V) are the residues of polymerization of the functional groups $R_4$ and $R_5$, respectively, in formula (III); and n is an integer from about 10 to about 500.

In certain embodiments, the zwitterionic phosphatidylserine moiety of the ZPS polymer is included, at least in part, in the polymer backbone.

In certain of these embodiments, the ZPS polymer has repeating units that include the following formula:

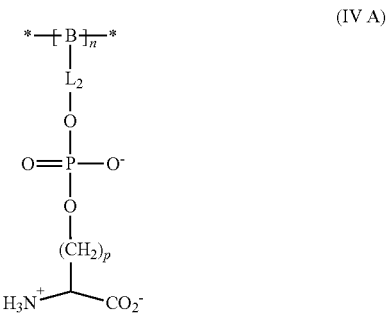

(IV A)

wherein $L_2$, p, and * are as described above for the polymer formula (IV), with the understanding that the point at which $L_2$ is coupled to B is the nitrogen of $N^+(R_1)$ (i.e., the atom in B to which $L_2$ is covalently coupled); and n is an integer from about 10 to about 500.

In other of these embodiments, the ZPS polymer has repeating units that include the following formula:

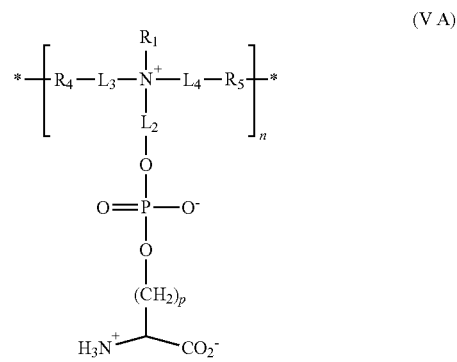

(V A)

wherein $R_1$, $R_4$, $R_5$, $L_2$, $L_3$, $L_4$, p, and * are as described above for the monomer of formula (III), with the understanding that $R_4$ and $R_5$ in formula (VA) are the residues of polymerization of the functional groups $R_4$ and $R_5$, respectively, in formula (III); and n is an integer from about 10 to about 500.

In certain embodiments, the invention provides a modified surface that comprises a polymer of formulae (II), (IV), (IVA), (V), or (VA). The modified surface can be the surface of artificial neural system, neuron-regeneration platform, neural sensor, cell-culture platform; non-fouling semi-conductor, battery, organic solar cell, biofuel cell, printed electronic circuit, organic light-emitting diode, actuator, electrochromism device, supercapacitor, chemical sensor, flexible transparent display, electromagnetic shield, antistatic coating, microwave-absorbent device, or radar-absorptive device.

In certain embodiments, the invention provides a bulk construct that comprises a polymer of formulae (II), (IV), (IVA), (V), or (VA). Representative constructs can be a medical, electronic, or marine device. In certain of these embodiments, the bulk construct is an artificial neural system, neuron-regeneration platform, neural sensor, cell-culture platform; non-fouling semi-conductor, battery, organic solar cell, biofuel cell, printed electronic circuit, organic light-emitting diode, actuator, electrochromism device, supercapacitor, chemical sensor, flexible transparent display, electromagnetic shield, antistatic coating, microwave-absorbent device, or radar-absorptive device.

ZPS star polymers and copolymers. In others aspects, the invention provides ZPS star polymers and ZPS copolymers that include ZPS repeating units.

These polymers include a core and a plurality of ZPS branches covalently coupled to the core. The cores of these polymers can be a small molecule, an oligomer, or a polymer having a star shape. In certain embodiments, these polymers can include three, four, five, or more ZPS branches. In certain of these embodiments, one or more of the ZPS branches may themselves be further branched. In certain embodiments, these polymers can further include terminal functional groups bound to the terminal end of the plurality of ZPS branches. Representative terminal functional groups are selected from OH, NH, $NH_2$, SH, $N_3$, CH=$CH_2$, C≡CH, COOH, CHO, imidoester, haloacetyl, hydrazide, alkoxyamine, aryl azide, diazirines, maleimide, carbodiimide, N-hydroxysuccinimide (NHS), thiazolidine-2-thione, pyridyldisulfide, difluorinatedcyclooctyne, Staudinger reagent pairs, isocyanate, isothiocyanate, thioether, sulfhydryl, hydrazine, hydroxymethyl phosphine, sulfo-NHS ester, pentafluorophenyl ester, sulfonylazide, and 5H-dibenz[b,f] azepine and their derivatives.

ZPS copolymers: hydrophobic and hydrophilic constitutional units. In further aspects, the invention provides ZPS copolymers that include ZPS repeating units and hydrophobic and/or hydrophilic constitutional units.

In certain embodiments, the copolymer is a random, diblock, or hyperbranched copolymer that includes ZPS repeating units (e.g., poly(ZPS)).

Representative block copolymers include at least one ZPS component block (A); and at least one hydrophobic block (B). In certain embodiments, the copolymer further comprises a hydrophilic block (C) or a second hydrophobic block (C). Block copolymers of the invention include AB diblock copolymers, ABC triblock copolymers, ABA triblock copolymers, BAB triblock copolymers, linear or star-shape multiblock $(AB)_n$ copolymers, Miktoarm block copolymers $(AB_n$ or $A_nB)$, and mixtures thereof. In certain embodiments, the copolymer further comprises neutral hydrophilic repeating units (e.g., alkylene oxide repeating units, such as ethylene oxide repeating units).

In certain embodiments, the copolymer includes a ZPS component that comprises a repeating unit derived from a ZPS monomer (e.g., an ZPS monomer of the invention having formulae (I) or (III)), and a hydrophobic component that comprises a repeating unit derived from a hydrophobic monomers.

Representative hydrophobic repeating units may be derived from acrylic acids and esters, alkyl acrylic acids and esters, acrylamides, alkyl acrylamides, polysiloxane repeating units, polyester repeating units, polyurethane repeating units, polystyrene repeating units, and fluorinated derivatives thereof.

In certain embodiments, the copolymer includes a ZPS component that comprises repeating units derived from a ZPS monomer (e.g., a ZPS monomer of the invention having formulae (I) or (III)), a hydrophilic component that comprises repeating units derived from a hydrophilic monomer, and optionally a hydrophobic component that comprises repeating units derived from a hydrophilic monomer. In certain of these embodiments, the hydrophilic repeating units comprise ZPS moieties. In other embodiments, the hydrophilic repeating unit can be a polyhydroxyethylmethacrylate (PHEMA), polyethylene glycol (PEG), polycarboxybetaine (PCB), polysulfobetaine (PSB), polyphosphobetaine (PPB), polyphosphorylcholine (PPC), polyacrylamide (PAA), poly(2,3-dihydroxypropyl methacrylate) (PDHPM), poly(N-isopropylacrylamide) (PNIPAM), polyacrylamide (PAM), poly(2-oxazoline), poly (acrylic acid), polymethacrylate (PMA), poly(vinyl alcohol) (PVA), poly(vinylpyrrolidone) (PVP), polyelectrolyte, polysaccharide, polyamide, and miscellaneous hydrophilic polymers, peptide-based materials and copolymers of two or more hydrophilic monomers.

ZPS polymeric surface coatings, bulk materials, and stand-alone materials

In other aspects, the present invention provides ZPS polymeric surface coatings, ZPS polymeric bulk materials, and ZPS polymeric stand-alone materials. In certain embodiments, the ZPS polymeric surface coatings, bulk materials, and stand-alone materials are prepared from ZPS monomers and polymers and copolymers prepared from ZPS monomers.

ZPS polymers can be attached to surfaces (e.g., medical devices, sensors, membranes, ships and marine structures) via "graft-from" or "graft-to" methods to render the surfaces nonfouling. ZPS polymers can be also blended with or into bulk materials (e.g., silicone). Surface coating can be on flat or nano/micro-particle surfaces. ZPS polymers can also be prepared into stand-alone low-fouling and high-strength materials and devices for medical and marine applications via (i) unique backbones such as silicone, fluorinated, urethane, imide, amide and (ii) strong interactions such as multiple hydrogen bonds, and (iii) interpenetrating networks.

ZPS polymeric surface coatings. The present invention provides ZPS polymeric surface coatings. In certain embodiments, the surface coating comprises a ZPS polymer (oligomer) or ZPS copolymer of the invention as described herein (e.g., a polymer of formulae (II), (IV), (IVA), (V), or (VA)).

The surfaces coated with the ZPS polymers and copolymers have nonfouling properties. Nonfouling properties of the surfaces can be evaluated by fibrinogen adsorption and cell adhesion. In certain embodiments, surfaces of the invention have fibrinogen adsorption less than about 200 $ng/cm^2$. In other embodiments, surfaces of the invention have fibrinogen adsorption less than about 100 $ng/cm^2$. In further embodiments, surfaces of the invention have fibrinogen adsorption less than about 50 $ng/cm^2$. In other embodiments, surfaces of the invention have fibrinogen adsorption less than about 30 $ng/cm^2$. In further embodiments, surfaces of the invention have fibrinogen adsorption less than about 20 $ng/cm^2$. In other embodiments, surfaces of the invention have fibrinogen adsorption less than about 10 $ng/cm^2$. In certain embodiments, surfaces of the invention have fibrinogen adsorption less than about 5 $ng/cm^2$.

In certain embodiments, the surfaces are coated with a ZPS polymer or copolymer prepared from one or more ZPS monomers selected from the polymerizable groups comprising of, but not limited to ZPS acrylates, ZPS acrylamides, ZPS methacrylates, ZPS methacrylamides, ZPS vinyl compounds, ZPS epoxides and mixtures thereof. Representative ZPS monomers include those described herein, including ZPS monomers of formulae (I) and (III).

In certain embodiments, the ZPS polymer or copolymer is a random, a multiblock, or a hyperbranched copolymer comprising a poly(ZPS). In other embodiments, the ZPS polymer or copolymer is an interpenetrating ZPS polymer network.

In certain embodiments, the ZPS polymer or copolymer is has surface adhesive groups (e.g., DOPA, thiol, silane, click chemistry, hydrophobic, hydrophilic, and charged groups).

The surfaces coated with the ZPS polymers and copolymers can be prepared by attaching the ZPS polymer or copolymers to a substrate surface via covalent interactions, physically hydrophobic-hydrophobic, charge-charge, and hydrogel-bonding interactions, or their combinations of chemical and physical interactions.

The surface coated with the ZPS polymers or copolymers can be prepared by grafting the ZPS polymers from the substrate surface ("grafted from") (e.g., preparing the polymeric surface by forming the polymer or copolymer by polymerizing suitable monomers in the presence of the substrate) or can be prepared by grafting the ZPS polymers to the substrate surface ("grafted to") (e.g., preparing the polymeric surface by coupling the pre-formed polymer or copolymer to the substrate).

In certain embodiments, the ZPS polymers and copolymers are grafted from the substrate by polymerization methods, such as atom-transfer radical-polymerization (ATRP), reversible addition-fragmentation chain-transfer polymerization (RAFT), or photoinferter polymerization.

In certain embodiments, the ZPS polymers and copolymers are grafted to the substrate by conjugation methods, such as click chemistry, DOPA conjugation chemistry, or self-assembled monolayer (SAM) via thiol or silane.

The ZPS polymeric surface coatings can be applied to a variety of substrates (e.g., substrate surfaces). In certain embodiments, the surface is all or part of biomedical device. Representative biomedical devices include catheters, ear drainage tubes, feeding tubes, glaucoma drainage tubes, hydrocephalous shunts, keratoprosthesis, nerve guidance tubes, tissue adhesives, x-ray guides, artificial joints, artificial heart valves, artificial blood vessels, pacemakers, left ventricular assist devices (LVAD), artery grafts, vascular grafts, stents, intravascular stents, cardiac valves, joint replacements, blood vessel prostheses, skin repair devices, cochlear replacements, contact lenses, artificial ligaments and tendons, dental implants, and tissue scaffolds for regenerative tissue engineering. In certain embodiments, the device is a contact lens.

In certain embodiments, the surface is all or part of a particle. Representative particles include metal, metal oxide, ceramic, synthetic polymer, natural polymer, silicon dioxide, crystal, and semiconductor material particles. In certain embodiments, the particle is a biomolecule, such as a protein (e.g., an enzyme) or a nucleic acid (e.g., a DNA or a RNA). In other embodiments, the particle is a cell.

In certain embodiments, the surface is all or part of a membrane or a bio-separation membrane. Representative membranes include membranes used for protein purification, wastewater treatment, bioreactors, desalination of sea water, and water/oil purification.

In certain embodiments, the surface is on or forming all of a drug delivery vehicle, such as a gene delivery vehicle, an RNA delivery vehicle, or a protein delivery vehicle.

In certain embodiments, the surface is on or forming all or part of an implantable or subcutaneous sensor.

In certain embodiments, the surface is on or forming all or part of a tissue scaffold.

ZPS polymeric bulk materials. The present invention provides ZPS polymeric bulk materials. In certain embodiments, the bulk materials comprises a ZPS polymer (oligomer) or ZPS copolymer of the invention as described herein (e.g., a polymer of formulae (II), (IV), (IVA), (V), or (VA)). In certain embodiments, the materials are prepared by a polymerizing or copolymerization process using a monomer of the invention as described herein (e.g., a monomer of formulae (I) or (III)).

In certain embodiments, the bulk material is obtained by blending of one or more ZPS polymers or copolymers with one or more other polymers, such as polyesters, polycarbonates, polyurethanes, polyureas, polysulfides, polysulfones, polyimides, polyepoxies, aromatic polyesters, cellulosics, fluoropolymers, polyacrylics, polyamides, polyanhydrides, polyethers, vinyl polymers, phenolics, elastomers, and other addition polymers.

In other embodiments, the bulk material comprises an interpenetrating ZPS polymer network and one or more other polymers, such as polyesters, polycarbonates, polyurethanes, polyureas, polysulfides, polysulfones, polyimides, polyepoxies, aromatic polyesters, cellulosics, fluoropolymers, polyacrylics, polyamides, polyanhydrides, polyethers, vinyl polymers, phenolics, elastomers, and other addition polymers.

ZPS polymeric standalone materials. The present invention provides ZPS polymeric standalone materials. In certain embodiments, the materials comprise a ZPS polymer (oligomer) or ZPS copolymer of the invention as described herein (e.g., a polymer of formulae (II), (IV), (IVA), (V) or (VA)). In certain embodiments, the materials are prepared by a polymerizing or copolymerization process using a monomer of the invention as described herein (e.g., a monomer of formula (I) or (III)).

In certain embodiments, the ZPS polymeric standalone materials are nonfouling materials and have high mechanical strength. In certain of these embodiments, the standalone material is a nonfouling material having protein adsorption less than about 30, less than about 50, or less than about 100 $ng/cm^2$, having tensile/compressive strengths greater than about, 0.2, greater than about 0.5, or greater than about 1.0 MPa.

In certain embodiments, the ZPS polymeric standalone material is a ZPS polymer network that is reinforced by introducing (a) dipole-dipole interactions such as cyano groups (C≡N) and (b) hydrogen donors/acceptors such as amide group (—(NH)—(C=O)—), multiple amide groups ((—(NH)—(C=O)—)$_n$ (n=1-5)), urethane group (—(NH)—(C=O)—O—), multiple urethane groups ((—(NH)—(C=O)—O—)$_n$ (n=1-5)), urea group (—(NH)—(C=O)—(NH)—), multiple urea groups ((—(NH)—(C=O)—(NH)—)$_n$ (n=1-5)), and their combinations. These groups can be derived from ZPS monomers and ZPS (random- or block-) copolymers. These groups can be in the polymer backbone or polymer pendant group.

The ZPS polymer networks can be reinforced with backbones in a ZPS monomer or a ZPS polymer, such as polyacrylate, polymethacrylate, polyacrylamide, polymethacrylamide, polyamide, polydimethylsiloxane, polyethylene, polypropylene, polystyrene, polytetrafluoroethylene, polyisobutene, polyesters, polycarbonates, polyurethanes, polyureas, polysulfides, polysulfones, polyimides, polyepoxies, polyanhydrides, polyethers, and other condensation/addition polymers. In certain embodiments, the ZPS polymer network is reinforced by any combination of the above.

In certain embodiments, the ZPS polymer can be form copolymers with other polymers or composites, such as polyesters, polycarbonates, polyurethanes, polyureas, polysulfides, polysulfones, polyimides, polyepoxies, aromatic polyesters, cellulosics, fluoropolymers, polyacrylics, polyamides, polyanhydrides, polyethers, vinyl polymers, phenolics, elastomers, and other addition polymers. Fiber, clays, nanotubes and other inorganic objects can be added to increase mechanical properties of these materials.

The ZPS standalone materials of the invention can be formed into an object by a variety of methods, such as injection molding, blow molding, extrusion molding, calendaring molding, flow casting, compression molding, prevarication molding, and 3D printing.

The ZPS standalone materials of the invention can be used in biomedical/biotechnological, consumer product, engineering/marine, therapeutics/diagnostics applications such as catheters, ear drainage tubes, feeding tubes, glaucoma drainage tubes, hydrocephalous shunt, keratoprosthesis, nerve guidance tubes, tissue adhesive, x-ray guide, an artificial joint, artificial heart valve, artificial blood vessel, pacemaker, left ventricular assist device (LVAD), artery graft, vascular grafts, stent, intravascular stent, cardiac valves, joint replacements, blood vessel prostheses, skin repair devices, cochlear replacements, contact lenses, artificial ligaments and tendons, dental implants and tissue scaffolds for regenerative tissue engineering, drug delivery, gene delivery, RNA delivery, protein delivery, marine and engineering devices/objects (e.g., membranes, tubes, pipes, containers, or plates).

In certain embodiments, the standalone materials can be used in marine products such as marine vessel hulls, marine structures, bridges, propellers, heat exchangers, periscopes, sensors, fish nets, cables, tubes/pipes, containers, membranes, and oil booms.

In certain embodiments, the standalone materials can be conjugated to a biomaterial. Representative biomaterials include nucleic acids (e.g., a gene, DNA, RNA), proteins (e.g., enzymes, antibody or functional fragment thereof), peptides, lipids, cells or microorganisms, solid nanoparticles (iron oxide, silica, quantum dot or gold nanoparticles), or used for protection against dehydration on skin by surfactants.

ZPS Polymeric Hydrogels

The present invention provides ZPS polymeric hydrogels. In certain embodiments, the hydrogel comprises a crosslinked ZPS polymer (oligomer) or ZPS copolymer of the invention as described herein (e.g., a polymer of formulae (I), (IV), (IVA), (V), or (VA)).

In certain embodiments, the hydrogel is prepared by a polymerizing or copolymerization process using a monomer of the invention as described herein (e.g., a monomer of formula (I) or (III)).

ZPS polymeric hydrogels can be created from ZPS monomers and various crosslinkers, including degradable or non-degradable ZPS crosslinkers. ZPS star polymers can be prepared by forming hydrogels (e.g., via click chemistry). These hydrogels can be in the form of bulk hydrogels or pellet hydrogels. These hydrogels can be used as implantable materials and devices to reduce capsule formation and as media to protect, expand, preserve and differentiate various cells (e.g., stem cells, immune cells, islets, platelets and cardiomyocytes) in controlled manners. Pellet and star hydrogels can be injectable along with biologics (e.g., various cells and tumor for tumor vaccine).

In certain embodiments, the ZPS hydrogel is a crosslinked hydrogel prepared from one or more ZPS monomers (e.g., a monomer of formula (I) or (II)) using one or more crosslinkers.

In other of these embodiments, the crosslinker is a multifunctional zwitterionic crosslinker that includes carboxybetaine, sulfobetaine, or phosphobetaine moieties.

In further of these embodiments, the crosslinker is a multifunctional crosslinker, such as N,N'-methylenebisacrylamide (MBAA), polyethylene glycol (PEG) diacrylate or diacrylamide, or PEG dimethacrylate or dimethacrylamide.

In certain embodiments, the hydrogel is prepared using a bifunctional ZPS crosslinker. In other embodiments, the hydrogel is prepared using a degradable or non-degradable crosslinker. In further embodiments, the hydrogel is prepared using a degradable, zwitterionic disulfide crosslinker. In other embodiments, hydrogel is prepared using peptide based crosslinker that can be degraded by enzymes or suitable agents.

The ZPS hydrogels of invention can be prepared by free radical mediated polymerization techniques, such as thermo-, photo-, or redox.

The preparation of a representative ZPS hydrogel of invention is described in Example 4. Protein adsorption and cell adhesion to the representative ZPS hydrogel is described in Example 4.

The ZPS hydrogels of invention can be used for biosensors and biomedical devices, vascular grafts, intravascular stents, cardiac valves, joint replacements, cell preservation/expansion/differentiation, drug delivery platforms, ship hulls, marine structures/equipment, and other materials and devices that come into contact with physiological environments.

In certain embodiments, the ZPS hydrogel is a star hydrogel. Star hydrogels can be prepared from a polymer having a core and a plurality of ZPS based or zwitterionic branches covalently coupled to the core. Representative cores include one of a small molecule, oligomer, or polymer of or star shapes with three, four, five or more branches.

In certain embodiments, the hydrogel is crosslinked by a degradable crosslinker that can be selectively degraded (i.e., under specific conditions). The degradable crosslinker can be selected from peptide crosslinkers, polysaccharide crosslinkers, anhydride crosslinkers, disulfide crosslinkers, and polyester crosslinkers. For certain of these embodiments, the hydrogel can be hydrolyzed or digested by enzymes.

In certain embodiments, the star hydrogel branch polymer comprises terminal functional groups bound to the terminal end of the branches (e.g., terminal end of plurality of ZPS or zwitterionic branches). Representative terminal functional groups include OH, NH, $NH_2$, SH, $N_3$, $CH=CH_2$, CECH, COOH, CHO, imidoester, haloacetyl, hydrazide, alkoxyamine, aryl azide, diazirine, maleimide, carbodiimide, N-hydroxysuccinimide (NHS), thiazolidine-2-thione, pyridyldisulfide, difluorinatedcyclooctyne, Staudinger reagent pairs, isocyanate, isothiocyanate, thioether, sulfhydryl, hydrazine, hydroxymethyl phosphine, sulfo-NHS ester, pentafluorophenyl ester, sulfonylazide, and 5H-dibenz[b,f]azepine.

In certain embodiments, the hydrogel comprises a first polymer/copolymer (first star hydrogel) bound to one or more second polymer/copolymers (second star hydrogel). The hydrogel can be used as an injectable hydrogel. In certain of these embodiments, the first polymer is bound to the one or more second polymers by a terminal functional group.

The star hydrogel can be combined with zwitterionic hydrogels and formed as a pellets of various size in specific templates or through mechanical reduction (e.g., blender). These pellet hydrogels can be used as injectable hydrogels with or without biological contents.

The ZPS star hydrogels of the invention can be made by (a) synthesizing ZPS or zwitterionic branches by ATRP, RAFT, ROP, condensation, Michael addition, branch generation/propagation reaction, and (b) reacting the ZPS or zwitterionic branches with a core to provide the star polymer. In certain embodiments, the method further comprises functionalizing the terminal end of the ZPS or zwitterionic branches by "click" reaction, thiol exchange reaction, or reductive reaction.

In certain embodiments, the ZPS hydrogel is a microgel. The microgels of the invention are micron-scale, crosslinked hydrogels having dimensions between about 1 micron ($10^{-6}$ m) and 1 mm ($10^{-2}$ m) composed of ZPS based monomers and supported by any crosslinking chemistry.

Microgels of the invention can be prepared by a variety of methods using a functionalized ZPS monomer, oligomer, or polymer, in which:
 (a) one of a reactive pair selected from an azide and an alkyne, an azide and an alkene, a thiol and a maleimide, a thiol and an alkene, a thiol and a disulfide, or any other "click", bioorthogonal, or other reactive pair;
 (b) positioned at the terminus of the polymeric structure(s) or along the backbone;
 (c) integrates a peptide, nucleic acid, protein, antibody, nanoparticle, microparticle, micelle, liposome, polymersome, drug, drug precursor, or other therapeutic species or drug delivery modality, for surgical applications, therapeutic applications, wound-healing applications, drug delivery formulations, cell storage and preservation, or regenerative medicine.

In certain embodiments, the microgel comprises a mixture of ZPS monomers or polymers and other classes of ionic or non-ionic nonfouling monomers or polymers, or a copolymer of ZPS based polymers and other classes of ionic or non-ionic monomers.

For the microgels, crosslinking is achieved using any combination of physical and/or chemical mechanisms, which in certain embodiments include:
 (a) chemical crosslinkers of any structure that are copolymerized with the monomers via a radical-mediated reaction, including commercially available crosslinkers based on polyethylene glycol (PEG), oligoethylene glycol (OEG) or other structures or groups, terminated with two or more acrylate, methacrylate, acrylamide, maleimide or similar reactive groups, or custom synthesized crosslinkers incorporating any functional, reactive, or degradable groups. Optional degradable groups may be selected from disulfide bonds, esters, anhydrides, enzymatically cleavable peptides (such as the GPQGIWCG motif), or chemistries responsive to external stimuli;
 (b) bioorthogonal crosslinking chemistries and 'click' chemistries, such as azide/alkyne (including SPAAC) and thiol-ene chemistries, whether through inclusion as functional groups in the main polymer chain(s) or architectures or as separate crosslinking molecules;
 (c) physical interactions of any type including ionic interactions, hydrogen bonding, hydrophobic interactions, interactions with biomolecules or nanoparticles of a natural or synthetic origin, or any other reversible or nonreversible physical interactions; and
 (d) any combination of the crosslinking mechanisms noted above.

In certain embodiments, the microgel is prepared using bifunctional ZPS crosslinking molecule, oligomer or polymer incorporating one or more ZPS moieties or a mixture of these molecules.

In certain embodiments, the microgel is prepared using zwitterionic (carboxybetaine, sulfobetaine or phosphobetaine) crosslinking molecule, oligomer or polymer incorporating one or more zwitterionic moieties or a mixture of these molecules. These crosslinkers may incorporate degradable groups, such as disulfide bonds, esters or stimuli-responsive groups or degradable peptides.

In certain embodiments, the invention provides a material formed from two or more assembled microgels, as described above, wherein the interactions between each discrete microgel result in bulk material with unique properties. These materials can include other ingredients, such as small molecule drugs, peptides, biomolecules, nanoparticles, cells or tissues.

In certain embodiments, the microgels and assemblies described above are produced from microgels having finite dimensions as a result of the polymerization method, for example, microemulsion polymerization.

In other embodiments, the microgels are derived from the (bulk) hydrogels described above or the star hydrogels described above, further sized to a finite dimension after polymerization, using any processing step to grind, extrude, mince, cut, or pellet the hydrogels to discrete units of finite size.

The microgels and assemblies described above can be dried or lyophilized (freeze-dried) to a dehydrated powder for storage, transport, use, or sterilization. The microgel powder can be rehydrated with any aqueous fluid, including water, saline or ionic solutions, cell growth or preservation media containing or not containing cells, or any other physiologically relevant solution that may contain therapeutic drugs, therapeutic proteins, therapeutic nucleic acids, cells, nanoparticles, or microparticles.

The ZPS star hydrogels and microgels and their assemblies and/or partially or fully dried or rehydrated compositions of these, have the following uses:
 (a) materials with non-Newtonian behavior (e.g., that exhibits viscoelastic, rheopectic, thixotropic, shear thickening (dilatant), shear thinning (pseudoplastic), and/or Bingham plastic properties);
 (b) self-healing materials and/or shape memory materials, or similar classes of 'smart' materials that can repair damage or recover their properties after damage or external stimuli; and
 (c) antifouling materials or surface coatings to prevent nonspecific protein or other biomolecule adsorption, e.g., for marine applications, drug delivery platforms, biosensors and other medical devices, vascular grafts, intravascular stents, cardiac valves, joint replacements, and other materials and devices that come into contact with physiological environments.

The ZPS star hydrogels and microgels and their assemblies can be used as an injectable or spreadable material for biomedical applications, particularly in applications requiring non-Newtonian fluid properties and high biocompatibility:
 (a) injectable or spreadable materials capable of mechanical support, such as those used in cosmetic or reconstructive surgery, blood vessel prostheses, skin repair devices, cochlear replacements, injectable vitreous substances, artificial cartilage, artificial fat, collagen-mimics and other soft tissue-mimics or supports;
(b) injectable or spreadable materials with desirable or specific biological interactions with a surface or tissue, particularly when nonspecific interactions should be avoided or a desired balance of nonspecific/specific interactions must be achieved; and
(c) injectable or spreadable carriers to deliver and/or protect or shield drugs, biomolecules (e.g., nucleic acids, peptides, proteins, polysaccharides), cells (e.g., pancreatic islets, cardiovascular cells, stem cells, T cells, blood cells), nanoparticles or microparticles (e.g., PLGA/drug formulations), micelles, liposomes, polymersomes, or other therapeutic species or drug delivery modalities, for surgical applications, therapeutic applications, wound healing, and drug delivery formulations.

The ZPS star hydrogels and microgels and their assemblies can be used as a scaffold, matrix, or substrate for the growth, maintenance or expansion of cells and tissues, in which the cells and microgel constructs can be grown using any culture method or apparatus including any type of bioreactor, and can be derived from lineages including:
(a) pluripotent and multipotent stem and progenitor cells, including:
  (i) embryonic stem cells (ESCs), tissue-derived stem cells (e.g., from skin, blood, or eye), hematopoietic stem and progenitor cells (HSPCs) derived or purified from umbilical cord blood or bone marrow, mesenchymal stem cells, or induced pluripotent stem cells (iPSCs),
  (ii) genetically modified or transfected stem and progenitor cells, and
  (iii) cancer stem cells (CSCs);
(b) hematopoietic cells typically circulating in human blood, including red blood cells (erythrocytes), white blood cells (leukocytes) and platelets (thrombocytes);
(c) immune cells and progenitors or differentiated lineages thereof, including:
  (i) T cells expressing the CD8 surface glycoprotein, particularly including naïve cytotoxic T lymphocytes (CTLs) and differentiated or activated lineages thereof including central memory T cells,
  (ii) T cells expressing the CD4 surface glycoprotein particularly including naïve helper T lymphocytes, and differentiated or activated lineages thereof including TH1, TH2, TH9, TH17, TFH, Treg and central memory (TCM) T cells,
  (iii) regulatory T cells (TREG) from any source, either natural Tregs or induced Tregs,
  (iv) natural killer T cells (NKT) cells,
  (v) chimeric antigen receptor T cells (CAR-T),
  (vi) genetically modified T cells;
(d) B cells, dendritic cells, and other antigen-presenting cells (APCs) or immune cells not specifically listed above;
(e) pancreatic islet or other insulin-producing cells and β cells useful in the treatment and management of diabetes;
(f) nervous system cells and progenitors;
(g) cardiovascular system cells and progenitors; and
(h) cells useful in the fields of immunotherapy, regenerative medicine, hematologic diseases or malignancies, or cancer vaccines or treatments.

The ZPS star hydrogels and microgels and their assemblies can be used as a biocompatible material, scaffold, formulation component or contacting material for any method of preserving cells or tissues or retaining their biological function for clinical or military utility, particularly for cell types that are difficult to preserve with conventional methods such as blood cells (e.g., platelets and red blood cells) for extended time periods, at room or low temperatures, in whole blood or preservation solutions, and with or without the presence of DMSO, glycerol, glycine betaine or other osmolytes or cryoprotectants.

The ZPS star hydrogels and microgels and their assemblies can be used for objects, devices, and components such as implantable biosensors; wound care devices, glues and sealants, a contact lens; a dental implant; an orthopedic device such as an artificial joint, an artificial bone, an artificial ligaments, and an artificial tendon; a cardiovascular device such as a catheter, an artificial valve, an artificial vessel, an artificial stent, LVADs, or a rhythm management device; gastroenterology devices such as feeding tubes, alimentary canal clips, gastro-intestinal sleeves, or gastric balloons; OB/Gyn devices such as implantable birth control devices or vaginal slings; nephrology devices such as anastomotic connectors or subdermal ports; neurosurgery devices such as nerve guidance tubes, cerebrospinal fluid drains or shunts, dermatology devices such as skin repair devices an ophthalmic device such as a shunt, otorhinolaryngology devices such as stents, cochlear implants, tubes, shunts or spreaders, an intra-ocular lense; an aesthetic implant such as a breast implant, a nasal implant, and a cheek implant; a neurologic implant such as a nerve stimulation device, a cochlear implant, and a nerve conduit; a hormone control implant such as a blood sugar sensor and an insulin pump; an implanted biosensor, an access port device; and a tissue scaffold pulmonic devices such as valves for management of COPD or artificial lungs; radiology devices such as radio-opaque or sono-opaque markers; or urology devices such as catheters or artificial urethrae.

In other aspects, the invention provides a substrate coated with a ZPS star hydrogel or microgel or microgel assemblies. Representative substrates include objects, devices, and components such as implantable biosensors; wound care devices, glues and sealants, a contact lens; a dental implant; an orthopedic device such as an artificial joint, an artificial bone, an artificial ligaments, and an artificial tendon; a cardiovascular device such as a catheter, an artificial valve, an artificial vessel, an artificial stent, LVADs, or and a rhythm management device; gastroenterology devices such as feeding tubes, alimentary canal clips, gastro-intestinal sleeves, or gastric balloons; OB/Gyn devices such as implantable birth control devices or vaginal slings; nephrology devices such as anastomotic connectors or subdermal ports; neurosurgery devices such as nerve guidance tubes, cerebrospinal fluid drains or shunts, dermatology devices such as skin repair devices an ophthalmic device such as a shunt, otorhinolaryngology devices such as stents, cochlear implants, tubes, shunts or spreaders, an intra-ocular lense; an aesthetic implant such as a breast implant, a nasal implant, and a cheek implant; a neurologic implant such as a nerve stimulation device, a cochlear implant, and a nerve conduit; a hormone control implant such as a blood sugar sensor and an insulin pump; an implanted biosensor, an access port device; and a tissue scaffold pulmonic devices such as valves for management of COPD or artificial lungs; radiology devices such as radio-opaque or sono-opaque markers; or urology devices such as catheters or artificial urethrae.

ZPS Polymeric Nanoparticles and Microparticles

In another aspect, the invention provides nano- and microparticles comprising the ZPS polymers and copolymers of the invention. The ZPS polymers and copolymers of the invention can be used to form nano- and microparticles in the form of nano- and microgels, micelles, liposomes, and polymersomes. They also can be used to coat solid particles such as quantum dots, iron oxides, silica, and gold for therapeutics or diagnostics. The ZPS polymers and copolymers of the invention can be associated with nano- and microparticles by covalent as well as non-covalent attachment.

In certain embodiments, particles having nanoscale dimensions are provided. The particles have a core having a surface having a plurality of ZPS polymers or copolymers grafted thereto or grafted therefrom. Representative particle cores include a metal, a metal oxide, a ceramic, a synthetic polymer, a natural polymer, a crystal, a semiconductor material, a graphene, a graphene oxide, an iron oxide, a silica, a quantum dot, a hydrogel, a liposome, a micelle, a carbon-based material, or a biomolecule.

ZPS Polymer and Copolymer Conjugates

In a further aspect, the invention provides ZPS polymer and copolymer conjugates. The ZPS polymers can be attached to biomolecules (e.g., proteins/peptides, nuclear acids, and sugars), other macromolecules, and cells by graft-to or graft-from methods to provide a variety of conjugates.

In certain embodiments, the ZPS polymer conjugate or copolymer conjugate is a ZPS polymer bioconjugate comprising one or more ZPS polymers coupled to a biomolecule. Suitable biomolecules include proteins, nucleic acids, glycoproteins, proteoglycans, and lipids. Suitable biomolecules include small molecule therapeutic agents (i.e., carbon-based therapeutic agents having a molecular weight less than about 1000 g/mole, preferably less than about 800 g/mole).

Representative proteins include enzymes, signaling proteins, hemostasis and thrombosis proteins, vaccines, complement system proteins, and antibodies, their functional fragments or characteristic portions. Representative signaling proteins includes hormones, cytokines, regulatory proteins, insulins, and PD-1/PD-L1/2 inhibitors.

In certain of these embodiments, the ZPS polymer conjugate or copolymer conjugate is a ZPS polymer or copolymer bioconjugate comprising one or more ZPS polymers or copolymers coupled to a biomolecule that has been modified, for example, a polymer-modified biomolecule. Exemplary polymer-modified biomolecules include biomolecules that have been modified with polyethylene glycol (PEG) polymers (e.g., the PEG moiety of these PEG-modified biomolecules can be in the polymer backbone or pendant from the polymer backbone). Representative polymer-modified biomolecules that are further modified by coupling one or more ZPS polymers or copolymers thereto are described in Example 5.

In other embodiments, the ZPS polymer conjugate or copolymer conjugate is a ZPS polymer or copolymer bioconjugate comprising one or more ZPS polymers coupled to a cell, a virus, or a bacterium.

The ZPS polymer conjugate or copolymer conjugate may be a delivery vehicle. Representative deliver vehicles include micelles, liposomes, or polymersomes, for therapeutic or diagnostic applications.

In certain embodiments, the invention provides a micelle, a liposome, a polymersome, or a particle that is self-assembled from a copolymer or a conjugated lipid of the invention comprising one or more ZPS polymers or copolymers.

In a further embodiment, the invention provides a composition comprising a ZPS polymer or copolymer conjugate and a pharmaceutically accepted carrier or diluent. In certain embodiments, the ZPS polymer and copolymers of the invention can be used as carrier or diluent for compositions.

The preparation and immunogenicity of a representative ZPS polymer protein conjugate is described in Example 7.

ZPS Polymer Nanogels and Nanocages

In another aspect, the invention provides ZPS polymer nanogels and nanocages. The ZPS polymers can be used to provide nanogels that chemically trap one or more other species, and nanocages that physically trap one or more other species.

In certain embodiments, the invention provides a nanogel for chemically encapsulating cargo, comprising one or more ZPS polymers or one or more ZPS copolymers.

In other embodiments, the invention provides a nanocage for physically encapsulating cargo, comprising one or more ZPS polymers or one or more ZPS copolymers.

Suitable cargo (e.g., species) that are chemically trapped by a nanogel or physically trapped by a nanocage include biomolecules, such as proteins, lipids, glycoprotein, cells, viruses, bacteria, and small molecules (e.g., therapeutic agents having molecular weights less than about 1000 g/mole, preferably 800 g/mole), or other biomolecules as described herein.

In certain embodiments, the nanogel or nanocages comprise a ZPS polymer or copolymer and one or more therapeutic agents.

In other embodiments, the nanogel or nanocage comprise a ZPS polymer or copolymer and one or more diagnostic agents.

In further embodiments, the nanogel or nanocage comprises a ZPS polymer or copolymer, one or more therapeutic agents, and one or more diagnostic agents.

Non-Zwitterionic Phosphatidylserine Monomers, Polymers, Copolymers, Compositions, Surfaces, and Methods for their Preparation and Use It will be appreciated that neutral phosphatidylserine (NPS) monomers, polymers, and copolymers, also referred to herein as non-zwitterionic phosphatidylserine (NZPS) monomers, polymers, and copolymers, are also within the scope of the present invention. Thus, in further aspects, the invention provides non-zwitterionic phosphatidylserine (NZPS) monomers, NZPS polymers and NZPS copolymers, methods for making the NZPS monomers, NZPS polymers, and NZPS copolymers, compositions and materials that include NZPS polymers and NZPS copolymers, and methods for using the NZPS monomers, NZPS polymers, and NZPS copolymers.

As used herein, the term "non-zwitterionic phosphatidylserine monomer" or "NZPS monomer" refers to a polymerizable monomer or a pendant group of a homopolymer or copolymer that includes a phosphatidylserine moiety ($NH_2$—CH(—$CH_2O$—P(=O)($O^-$))—$CO_2H$ and its ionic forms).

A representative NZPS monomer has formula (VI):

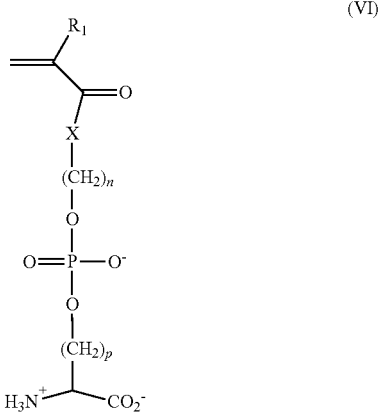

wherein, in certain embodiments, $R_1$ is selected from the group consisting of hydrogen, fluorine, trifluoromethyl, cyano, $C_1$-$C_{20}$ alkyl (preferably $C_1$-$C_6$ alkyl), and $C_6$-$C_{12}$ aryl, X is O or NH, n is an integer from 1 to 20 (e.g., 1, 2, 3, 4, 5, or 6), and p is an integer from 1 to 20 (e.g., 1, 2, 3, 4, 5, or 6).

The term "non-zwitterionic phosphatidylserine polymer" or "NZPS polymer" refers to a polymer (i.e., homopolymer or copolymer) having one or more pendant groups that include a phosphatidylserine moiety, as described above.

A NZPS polymer is prepared by polymerization of a monomer of formula (VI) and a NZPS copolymer is prepared by copolymerization a monomer of formula (VI) and a comonomer. These NZPS polymers (homopolymers, random copolymers, block copolymers) include repeating units having pendant phosphatidylserine (PS) moieties, as shown below:

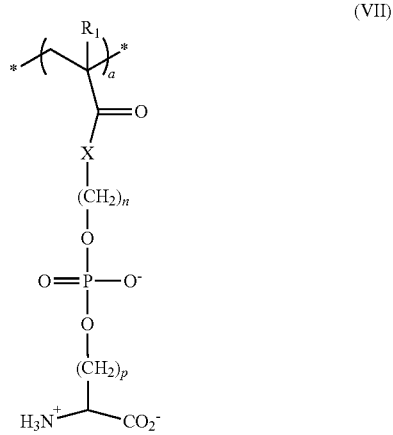

wherein, in certain embodiments, $R_1$, X, n, and p are as described above for the monomer of formula (VI), a is an integer from about 10 to about 500, and * indicates the point of attachment of the repeating unit to other repeating units in the polymer or copolymer, or the polymer terminal groups.

The NZPS monomers can be readily polymerized under standard polymerizing conditions to provide NZPS polymers.

It will therefore be appreciated that the entire description herein for ZPS monomers, ZPS polymers, ZPS copolymer, compositions that include ZPS polymers, surfaces that include ZPS polymers, and methods for using ZPS monomer, polymers and compositions, applies equally to NZPS monomers, polymers, compositions, surfaces, and methods.

Example 2 describes the preparation and characterization of a representative NZPS of the invention.

The preparation and immunogenicity of a representative NZPS polymer protein conjugate is described in Example 7.

Described herein are PS-mimetic polymerizable (NZPS) monomers, polymers derived from the monomers, and polymers attached to biomolecules, macromolecules, small molecules, particles, implants, devices, surfaces, coatings, and hydrogels. The biocompatible immunosuppressive biomaterials include the NZPS polymers, and their derivatives and precursors, for use with peptides, proteins, lipids, glycoproteins, biomacromolecules (such as, for example, cells, virus, bacteria), nanoparticles, microparticles, small-molecule drugs, any of which can be used in administration in the human body, including in conjunction with medical devices, prosthetics, implanted materials (including dental), organ transplant.

In one aspect, the polymerizable NZPS monomer and derivatives or precursors have the formula (VI) shown below:

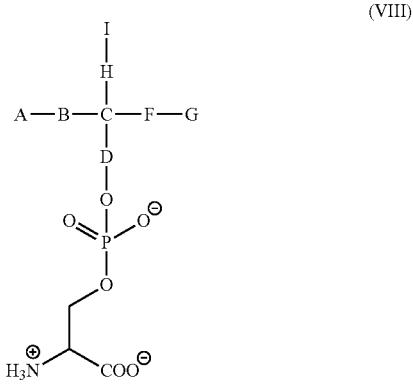

wherein

A, G, and I are functional groups that in certain embodiments render the monomer polymerizable, and are independently selected from H, F, Cl, Br, I, SH, protected thiols, $NH_2$, —NH— (secondary amine), N=C=O, protected NCO, N=C=S, COOH, activated ester, aldehyde, COSH, C(=S)SH, OCOOH, OCOSH, OC(=S)OH, SC(=O)SH, SC(=S)SH, N(C=O)$NH_2$, N(C=NH)$NH_2$, N(C=S)$NH_2$, δ-valerolactone, ε-caprolactone, $CH_2$=CH—C(=O)—O—, $CH_2$=CH—C(=O)—NH—, $CH_2$=CH—C(=O)—S—, CN, $CH_2$=C($CH_3$)—C(=O)—O—, $CH_2$=C($CH_3$)—C(=O)—NH—, OH, azides, alkynes, $C_6$-$C_{10}$ aryl groups, cyclic groups (isobornyl, cyclohexyl, cyclopentyl), fluoro (perfluorobutyl, perfluoroethyl) derivatives, or void (absent);

B, F, and H are selected independently from —$(CH_2)_x$—, where x is an integer from 0 to 20;

C cis selected from be C, N, Si, or void (absent); and

D is selected from $C(=O)(CH_2)_x$, —$(CH_2)_x$—, where x is an integer from 1 to 20;

Methods for preparing these monomers, polymers prepared from these monomers, and methods for using these polymers to attach them to or from nanoparticles, surfaces, coatings, and hydrogels, and their use for imparting immunosuppressive effects to these nanoparticles, surfaces, coatings, and hydrogels are also provided.

In another aspect, the NZPS polymers and copolymers are provided. These polymers and copolymers include repeating units. In certain embodiments, the repeating units of these polymers and copolymers have the formula (IX) shown below (less $R_2$ and $R_3$) (the repeating units would not include $R_2$ and $R_3$; however, macromonomers would and possibly also the polymers and copolymers):

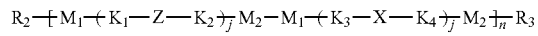

(IX)

with n repeating units -$M_1$-($K_1$—Z—$K_2$)$_j$-$M_2$-$M_1$-($K_3$—X—$K_4$)$_j$-$M_2$-, which includes j repeating units —$K_1$—Z—$K_2$— and j repeating units —$K_3$—X—$K_4$—.

In the above formula, $K_1$, $K_2$, $K_3$, and $K_4$ are independently selected from —$(CH_2)_x$—, —$(CH(CN))_x$—, —$C(=O)NH(CH_2)_x$—, —$C(=O)O(CH_2)_x$—, —$C(=O)OC(=O)O(CH_2)_x$—, —$(CH_2)_x$—O—$(CH_2)_x$—, and —$(CH_2)_x$—S—S—$(CH_2)_x$—, where x at each occurrence is an integer independently selected from 0 to 20, combinations thereof, or void (when substituent is absent);

$R_2$ and $R_3$ are independently selected from H, F, Cl, Br, I, OH, SH, protected thiols, $NH_2$, —NH— (secondary amine), N=C=O, N=C=S, COOH, COSH, C(=S)SH, OCOOH, OCOSH, OC(=S)OH, SC(=O)SH, SC(=S)SH, N(C=O)$NH_2$, N(C=NH)$NH_2$, N(C=S)$NH_2$, δ-valerolactone moiety, ε-caprolactone moiety, $CH_2$=CH—C(=O)—O—, $CH_2$=CH—C(=O)—NH—, $CH_2$=CH—C(=O)—S—, CN, $CH_2$=C($CH_3$)—C(=O)—O—, $CH_2$=C($CH_3$)—C(=O)—NH—, or void (when substituent is absent);

n is an integer from 5 to about 10,000.

j at each occurrence is an integer from 1 to about 1000.

$M_1$ and $M_2$ are independently selected from the group consisting of —O—$(CH_2)_n$—, —S—$(CH_2)_n$—, —C(=O)—$(CH_2)_n$—, —C(=S)—$(CH_2)_n$—, —C(=NH)—$(CH_2)$— and —NH—$(CH_2)_n$—, wherein n is an integer from 1 to 20; —$(CH_2)_x$—, —$(CH(CN))_x$—, —$C(=O)NH(CH_2)_x$—, —$C(=O)O(CH_2)_x$—, —$C(=O)OC(=O)O(CH_2)_x$—, —$(CH_2)_x$—O—$(CH_2)_x$—, and —$(CH_2)_x$—S—S—$(CH_2)_x$—, where x at each occurrence is an integer independently selected from 0 to 20, combinations thereof, or void (when substituent is absent); and Z and X are independently selected from the group consisting of the following formula:

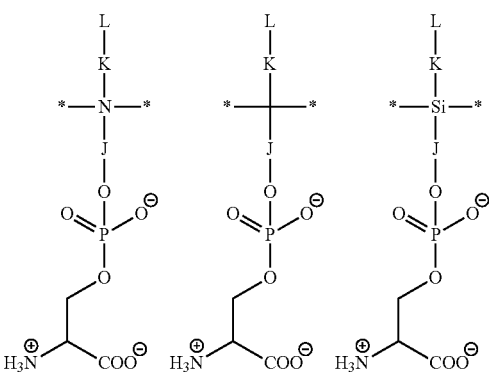

wherein L is independently selected from F, Cl, Br, I, SH, protected thiols, $NH_2$, —NH— (secondary amine), N=C=O, protected NCO, N=C=S, COOH, COSH, C(=S)SH, OCOOH, OCOSH, OC(=S)OH, SC(=O)SH, SC(=S)SH, N(C=O)$NH_2$, N(C=NH)$NH_2$, N(C=S)$NH_2$, δ-valerolactone, ε-caprolactone, $CH_2$=CH—C(=O)—O—, $CH_2$=CH—C(=O)—NH—, $CH_2$=CH—C(=O)—S—, CN, $CH_2$=C($CH_3$)—C(=O)—O—, $CH_2$=C($CH_3$)—C(=O)—NH—, OH, azides, alkynes, $C_6$-$C_{10}$ aryl groups, cyclic groups (isobornyl, cyclohexyl, cyclopentyl), fluoro (perfluorobutyl, perfluoroethyl) derivatives, or void;

K is selected independently from —$(CH_2)_x$—, where x is an integer from 0 to 20;

J is selected from $C(=O)(CH_2)_x$, —$(CH_2)_x$—, where x is an integer from 1 to 20; and

* is the point of attachment to $K_1$, $K_2$, $K_3$, and $K_4$ as shown in the

As used herein, the term "about" refers to ±5 percent of the specified value.

The following examples are provided for the purpose of illustrating, not limiting, the invention.

EXAMPLES

Preparation and Characterization of a Representative ZPS Monomer

In this example, the synthesis and purification of a representative polymerizable zwitterionic (ZPS) monomer are described.

An illustrative process to synthesize the polymerizable ZPS monomer of the present invention is shown below.

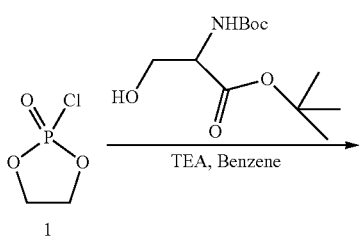

1

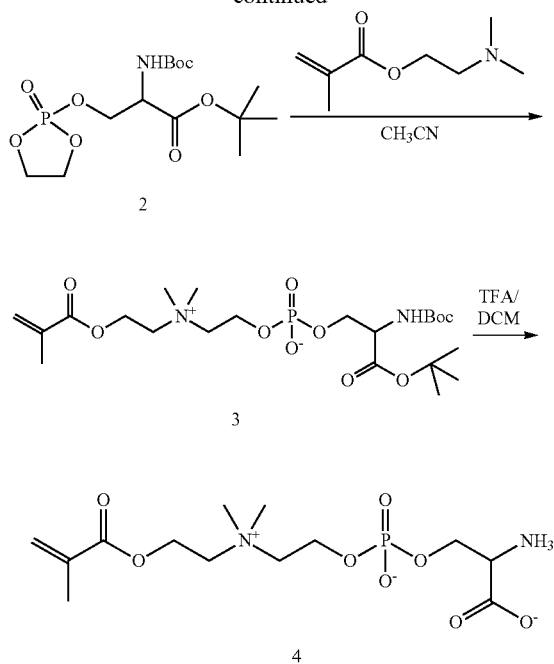

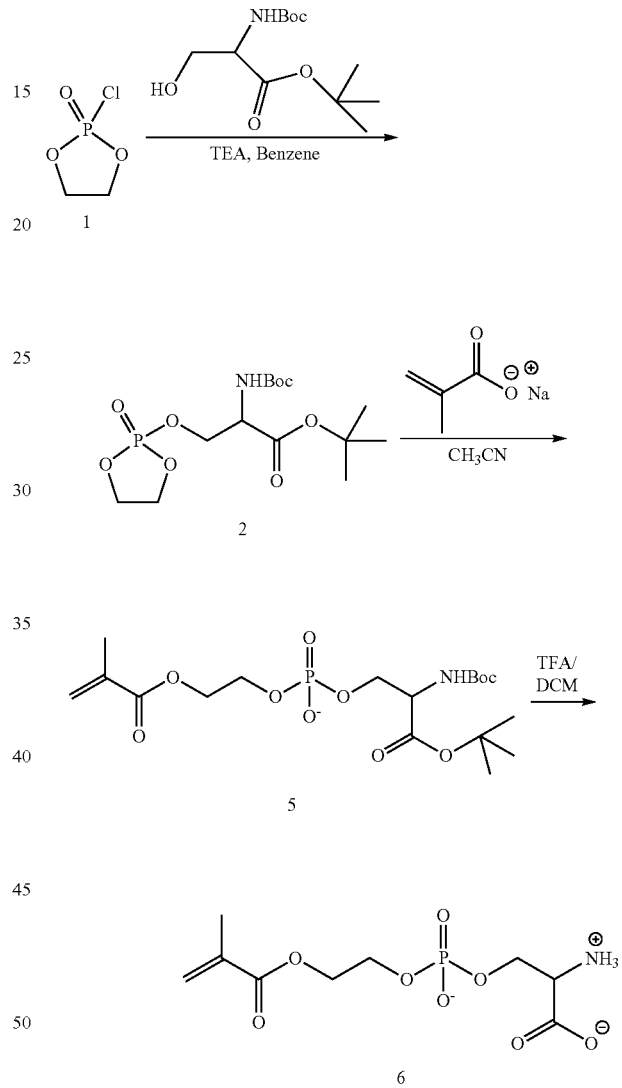

Synthesis of 3-(tert-butoxy)-2-((tert-butoxycarbonyl) amino)-3-oxopropyl (2-((2-(methacryloyloxy)ethyl)dimethylammonio)ethyl) phosphate (Compound 3). N-Boc-Ser-OtBu (1.0 gm, 3.82 mmol) was dissolved in 30 ml dry benzene and the solution was cooled to 0° C. Next, triethylamine (0.62 mL, 4.6 mmol) was added followed by dropwise addition of 2-chloro-2-oxo-1,3,2-dioxaphospholane 1 (0.42 mL, 4.6 mmol) in 10 mL dry benzene over a period of 30 minutes and then the reaction contents were stirred at room temperature for another 3 hours. After completion of reaction, diethyl ether was poured into the reaction mixture and the precipitated trimethylamine hydrochloride was filtered off. The filtrate was then concentrated under reduced pressure to give Compound 2 as an oil which was used in next step without further purification. Compound 2 was redissolved in 30 mL anhydrous acetonitrile and 2-(dimethylamino)ethyl methacrylate (1.45 mL, 8.8 mmol) was added. The reaction mixture was then stirred at 55° C. for 24 hours. The reaction contents were then concentrated under vacuum and purified by flash column chromatography to give compound 3 in 42% yield. $^1$H NMR (300 MHz, CDCl$_3$) δ 6.18 (s, 1H), 5.67 (s, 1H), 4.63-4.54 (m, 2H), 4.35-4.14 (m, 3H), 4.10-3.99 (m, 2H), 3.83-3.76 (m, 2H), 3.40-3.27 (m, 2H), 2.82 (s, 6H), 1.97 (s, 3H), 1.46 (d, J=11.7 Hz, 18H).

Synthesis of a representative ZPS monomer (Compound 4). Compound 3 (0.84 gm, 1.6 mmol) was dissolved in 5 mL dichloromethane and 30 mL trifluoroacetic acid was added. The reaction contents were stirred for 5 hours. After completion of the reaction, the reaction mixture was concentrated under vacuum to give a thick viscous liquid. The crude product was then crystallized with MeOH:diethyl ether (1:15) to give desired Compound 4 as white powder. $^1$H NMR (300 MHz, D$_2$O) δ 6.08 (s, 1H), 5.69 (s, 1H), 4.47-4.41 (m, 2H), 4.26-4.23 (m, 2H), 4.05-4.00 (m, 1H), 3.87-3.84 (m, 2H), 3.69-3.67 (m, 2H), 3.50-3.45 (m, 2H), 2.88 (s, 6H), 1.84 (s, 3H).

Example 2

Preparation and Characterization of a Representative Neutral PS Monomer

In this example, the synthesis and purification of a representative polymerizable neutral PS (NZPS) monomer are described. An illustrative process to synthesize the NZPS monomer is shown below.

Synthesis of Compound 5. N-Boc-Ser-OtBu (1.0 gm, 3.82 mmol) was dissolved in 30 ml dry benzene and the solution was cooled to 0° C. Next, triethylamine (0.62 mL, 4.6 mmol) was added followed by dropwise addition of 2-chloro-2-oxo-1,3,2-dioxaphospholane 1 (0.42 mL, 4.6 mmol) in 10 mL dry benzene over a period of 30 minutes and then the reaction contents were stirred at room temperature for another 3 hours. After completion of reaction, diethyl ether was poured into the reaction mixture and the precipitated trimethylamine hydrochloride was filtered off. The filtrate was then concentrated under reduced pressure to give Compound 2 as an oil which was used in next step without further purification. Compound 2 was redissolved in 30 mL anhydrous acetonitrile and sodium methacrylate (0.62 gm, 5.7 mmol) along with 18-crown-6 ether (0.14 gm, 0.53 mmol) was added to it. The reaction mixture was then stirred at 55° C. for 72 hours. After the reaction, the reactions contents were filtered, concentrated under vacuum and purified by flash column chromatography to give compound 5 in 71% yield. $^1$H NMR (300 MHz, CDCl$_3$) δ 6.15 (s, 1H), 5.57 (s, 1H), 4.41-4.27 (m, 2H), 4.24-4.04 (m, 4H), 3.86-3.78 (m, 1H), 1.95 (s, 3H), 1.46 (d, J=5.4 Hz, 18H).

Synthesis of representative neutral PS monomer (Compound 6). Compound 5 (1.2 gm, 2.65 mmol) was dissolved in 5 mL dichloromethane and 30 mL trifluoroacetic acid was added to it. The reaction contents were stirred for 5 hours. After completion of the reaction, the reaction mixture was concentrated under vacuum to give a thick viscous liquid. The crude product was then crystallized with MeOH:diethyl ether (1:20) to give desired Compound 6 as white powder. $^1$H NMR (300 MHz, D$_2$O) δ 6.11 (s, 1H), 5.66 (s, 1H), 4.34-4.15 (m, 5H), 4.10-3.97 (m, 2H), 1.85 (s, 3H).

Example 3

Non-Fouling Properties of Representative NZPS and ZPS Hydrogels

In this example, the non-fouling properties of Representative NZPS and ZPS hydrogels are described.
Preparation of ZPS Hydrogel ZPS hydrogels were fabricated by bulk photo-polymerization with a hydrogel aqueous solution containing ZPS monomer (0.67 g Milli-Q water, 330 mg), crosslinker N,N' methylenebis(acrylamide) (1 wt %, 3.3 mg) and photo-initiator 2-hydroxy-2-methylpropiophenone (0.33 mg). The hydrogel aqueous solution was placed between two glass slides separated by a 0.5 mm-thick polytetrafluoroethylene spacer, and was then photo-polymerized at room temperature for 30 mins. After polymerization, hydrogels were removed from the casts and soaked in PBS for three days to remove unreacted chemicals and reach the fully hydrated hydrogel network. Phosphate buffered saline was refreshed every 12 hours. Following the same protocol, MPC and NZPS hydrogels with the same crosslinking density were prepared.
Fibrinogen Adsorption Test Biopsy punches were used to punch the hydrated MPC, NZPS, and ZPS hydrogels into 5 mm-diameter disks. Hydrogel disks were placed into a 24 well-plate and incubated with 1 mL of 1 mg/mL fibrinogen in PBS buffer for 1 hour, followed by 5 washes with pure PBS buffer. Hydrogel disks were then transferred to new wells and incubated with 1 mL of horseradish peroxidase (HRP) conjugated anti-fibrinogen (1 μg/mL) in PBS buffer for 1 hour. All hydrogel disks were then transferred to new wells after 5 washes with pure PBS buffer. Next, 1 mL 1 mg/mL o-phenylenediamine (OPD) 0.1 M citrate phosphate pH 5.0 solution, containing 0.03% hydrogen peroxide was added. After 15 min incubation, the enzymatic reaction was stopped by adding an equal volume of 1 M HCL. The same procedure was conducted on of tissue culture polystyrene (TCPS) disks with the same surface area as the control. Absorbance value at 492 nm was recorded by a plate reader and was normalized to that TCPS sample. Average data were acquired from three specimens.

Figure 1:
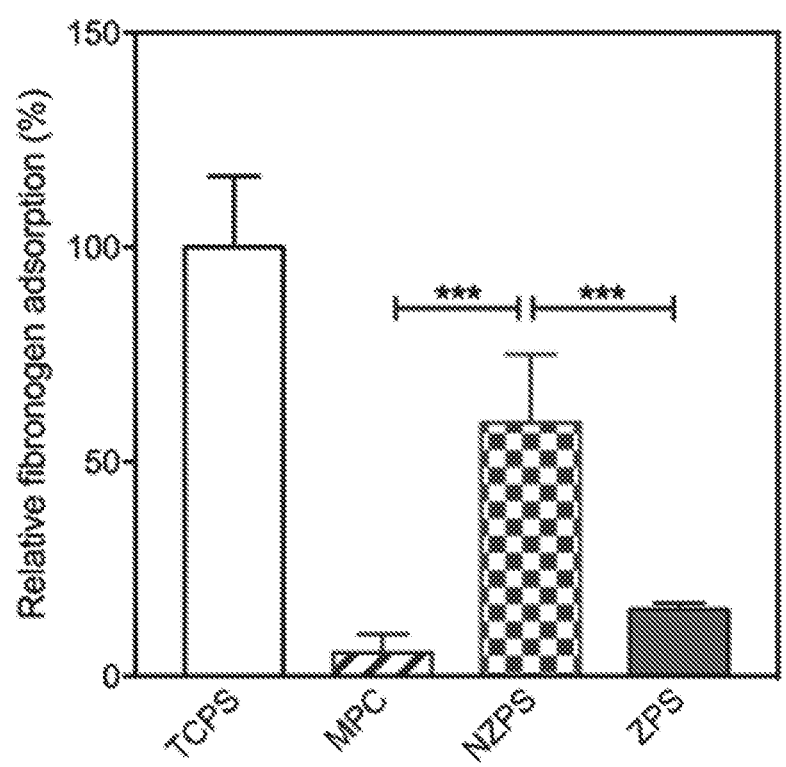
FIG. 1 compares relative fibrinogen adsorption (%) for MPC, NZPS, and ZPS hydrogel surfaces relative to control TCPS, as measured by ELSIA.

ZPS hydrogel disks exhibited an exceptional non-fouling property after 1 h incubation in a highly concentrated fibrinogen solution (10 mg/mL) by reducing 84.4% of adsorbed fibrinogen with respect to that of TCPS disks. In contrast, NZPS hydrogel disks only reduced 41% adsorbed fibrinogen compared to that of TCPS disks (FIG. 1).

Example 4

Immunosuppressive Effect of Representative NZPS and ZPS Nanogels

In this example, the immunosuppressive effect of representative NZPS and ZPS nanogels is described.
Preparation of MPC, NZPS, and ZPS Nanogels AOT (sodium bis(2-ethylhexyl) sulfosuccinate, 237 mg) and Brij 30 (poly(ethylene glycol) dodecyl ether, 459 mg) were added to a 20 mL glass vial to which a stir bar was added. The vial was sealed with a Teflon-lined septum cap and purged with dry nitrogen for 10 min. Nitrogen-deoxygenated hexane (10 mL) was then added to the vial under vigorous stirring. For the aqueous phase, monomers (MPC, NZPS, ZPS) and crosslinker (MBA) was dissolved in PBS buffer (pH 7.4, 250 μL) at a mole ratio of 95%:5%. Dry nitrogen was bubbled through the monomer solution for 2 min, after which the aqueous phase was slowly added to the organic continuous phase dropwise. The vial was sonicated to form a stable nanoemulsion. A 20% (w/v) solution of ammonium persulfate in deionized water (10 μL) was then added to the emulsion. After 5 min, polymerization was initiated by the addition of tetramethylethylenediamine (TEMED, 6 μL) and maintained at 4° C. under rapid magnetic stirring. After the 2 hr reaction, the organic solvent was removed by rotary evaporator and the nanogel was precipitated and washed with THF for three times. The nanogel was re-suspended in PBS buffer and purified with 100-KDa molecular weight cutoff centrifugal filters to remove the unreacted monomer and crosslinker.
Preparation of MPC, NZPS, and ZPS Nanogels Encapsulating FITC-BSA AOT (sodium bis(2-ethylhexyl) sulfosuccinate, 237 mg) and Brij 30 (poly(ethylene glycol) dodecyl ether, 459 mg) were added to a 20 mL glass vial to which a stir bar was added. The vial was sealed with a Teflon-lined septum cap and purged with dry nitrogen for 10 min. Nitrogen-deoxygenated hexane (10 mL) was then added to the vial under vigorous stirring. For the aqueous phase, FITC-BSA, monomers (MPC, NZPS, ZPS) and crosslinker (MBA) was dissolved in PBS buffer (pH 7.4, 250 μL) at a mole ratio of 95%:5%. Dry nitrogen was bubbled through the monomer solution for 2 min, after which the aqueous phase was slowly added to the organic continuous phase dropwise. The vial was sonicated to form a stable nanoemulsion. A 20% (w/v) solution of ammonium persulfate in deionized water (10 μL) was then added to the emulsion. After 5 min, polymerization was initiated by the addition of tetramethylethylenediamine (TEMED, 6 μL) and maintained at 4° C. under rapid magnetic stirring. After the 2 hr reaction, the organic solvent was removed by rotary evaporator and the nanogel was precipitated and washed with THF for three times. The nanogel was re-suspended in PBS buffer and purified with 100-KDa molecular weight cutoff centrifugal filters to remove the free FITC-BSA, unreacted monomer and cross-linker.
Immunosuppressive Effect RAW 264.7 cells ($10^5$/well) were exposed to MPC, NZPS, or ZPS nanogel solution at various concentration (10, 25, 50, 100, 200, 1000 μg/ml) for 18 hours. Then, these cells were stimulated by LPS solution (100 ng/mL) for another 48 hours, after which the cells were spun at 300 g for 10 min and the supernatant medium was collected for cytokine (TNF-α) analysis by ELISA. As shown in FIG. 2A, while the impact of NZPS and ZPS on the level of TNF-α are both dose-dependent, NZPS began to display its inhibition on TNF-α at a relatively low concentration, suggesting its strong immunosuppressive effect compared to that of ZPS.

Annexin V Blockade

To confirm that the immunosuppressive effect of NZPS and ZPS originates from the eat-me signal mediated by their PS head groups, the MPC, NZPS, or ZPS nanogel solution (100 μg/ml) was pre-incubated with Annexin V, a protein that has high affinity to the PS group and can block the eat-me signal, at various concentrations (0, 10, 25, 50, 100, 200 μg/ml) for 6 hours. Then RAW 264.7 macrophages ($10^5$/well) were then treated with these nanogel solution (100 μg/ml) for 18 hr followed by the stimulation of LPS (100 ng/mL) for 48 hr. The level of TNF-α secretion in the supernatant was measured by ELISA kit. As shown in FIG. 2B, with the concentration of Annexin V increased, the effect of NZPS and ZPS nanogel in reducing TNF-α secretion was dropping, revealing an effective blockade of their immunosuppressive effect. Notably, ZPS nanogel is less sensitive to the blocking effect of Annexin V, probably because the non-fouling property of ZPS could to some extent decrease the affinity of PS functional groups in ZPS to its receptors. This also explains why the immunosuppressive effect of ZPS is weaker than that of NZPS.

Cell Uptake

RAW 264.7 macrophages ($10^5$/well) were incubated with MPC, NZPS, and ZPS nanogel encapsulating FITC-BSA for 30, 60, 120, and 180 min, after which the cells were washed and lysed for the detection of recovered fluorescence. As shown in FIG. 2C, MPC displayed the minimal cell uptake due to its excellent non-fouling property while NZPS nanogel was quickly taken up by macrophages due to its mediation of eat-me signal. Compared to NZPS, the uptake of ZPS is slowed down due to its non-fouling property and reduced affinity to receptors. These results suggest that the unique zwitterionic structure of ZPS could achieve effective immunosuppression and good non-fouling performance simultaneously.

Example 5

Representative Poly(ZPS)- and Poly(NZPS)-Containing Bioconjugates

In this example, representative bioconjugates of the invention are described. In certain embodiments, the representative bioconjugate includes a ZPS polymer component. In other embodiments, the representative bioconjugate includes a NZPS polymer component.

In this example, the bioconjugate is an enzyme conjugate. The representative enzyme is a uricase. The polymers are covalently coupled to the enzyme, either directly or via linkers suitable for linking the polymer to enzyme.

In the representative bioconjugates shown below, the bioconjugates further include a poly(ethylene glycol) (PEG) moiety. In certain embodiments, these bioconjugates include PEG in the linker intermediate the enzyme and the PS polymer. In other embodiments, these bioconjugates include PEG as a pendant group from a polymeric backbone (e.g., derived from polymerization of PEGMA).

Preparation and Characterization of a Representative Poly (ZPS)-Block-Poly(PEGMA) Block Copolymer Containing Bioconjugate Synthesis of thiol group-terminated Poly(ZPS)-block-Poly(PEGMA) block copolymer. Reversible addition-fragmentation chain-transfer (RAFT) polymerization is used to prepare the block copolymer. Generally, the polymerization of ZPS monomer (6.7 g) is initiated by azobisisobutyronitrile (AIBN, 18 mg) in the presence of 2-(dodecylthiocarbonothioylthio)-2-methylpropionic acid (100 mg) as chain transfer agent (CTA). After 12 h of reaction, the polymerization is stopped and the obtained polymer, Poly(ZPS)-CTA, is purified by dialysis. Then Poly(ZPS)-CTA is used as macromolecular CTA for the polymerization of PEGMA monomer (molar ratio: CTA/PEGMA=1/50). After precipitation in excess ether, Poly(ZPS)-block-Poly(PEGMA)-CTA block copolymer is further purified by dialysis and lyophilization. The CTA moiety on the block copolymer is then converted into thiol group by using a mixture solution of hexylamine and triethylamine.

Preparation of Poly(ZPS)-Block-Poly(PEGMA)-Uricase Conjugate

Amine groups on uricase are first converted into maleimide groups by a bifunctional crosslinker, BMPS (N-maleimidopropyl-oxysuccinimide ester). Activated uricase (10 mg) is then mixed with thiol group-terminated Poly(ZPS)-block-Poly(PEGMA) copolymer (300 mg) in 4 ml of PBS. Poly(ZPS)-block-Poly(PEGMA)-Uricase conjugate is purified by diafiltration to remove excess polymers and unreacted uricase.

Preparation and Characterization of a Representative Poly (ZPS) and Poly(PEGMA) Polymers Containing Bioconjugate Synthesis of thiol group-terminated Poly(ZPS). Reversible addition-fragmentation chain-transfer (RAFT) polymerization is used to prepare the block copolymer. Generally, the polymerization of ZPS monomer (6.7 g) is initiated by azobisisobutyronitrile (AIBN, 18 mg) in the presence of 2-(dodecylthiocarbonothioylthio)-2-methylpropionic acid (100 mg) as CTA. After 12 h of reaction, the polymerization is stopped and the obtained polymer, Poly(ZPS)-CTA, is purified by dialysis. The CTA moiety on Poly(ZPS)-CTA is then converted into thiol group by using a mixture solution of hexylamine and triethylamine.

Synthesis of thiol group-terminated Poly(PEGMA). The polymerization of PEGMA (5 g) is initiated by azobisisobutyronitrile (AIBN, 18 mg) in the presence of 2-(dodecylthiocarbonothioylthio)-2-methylpropionic acid (100 mg) as chain transfer agent (CTA). After 12 h of reaction, the polymerization is stopped and the obtained polymer, Poly (PEGMA)-CTA, is purified by dialysis. The CTA moiety on Poly(PEGMA)-CTA is then converted into thiol group by using a mixture solution of hexylamine and triethylamine.

Preparation of Poly(ZPS) and Poly(PEGMA) Containing Bioconjugate.

Amine groups on uricase are first converted into maleimide groups by a bi-functional crosslinker, BMPS (N-maleimidopropyl-oxysuccinimide ester). Activated uricase (10 mg) is then mixed with thiol group terminated Poly(ZPS) (100 mg) in 4 ml of PBS. Poly(ZPS)-Uricase conjugate is purified by diafiltration to remove excess polymers and unreacted Uricase. A second conjugation step is carried out by mixing thiol group-terminated Poly(PEGMA) with Poly (ZPS)-Uricase. Poly(ZPS) and Poly(PEGMA) modified uricase are purified by diafiltration to remove excess polymers.

Representative bioconjugates described in this example have the following structures:
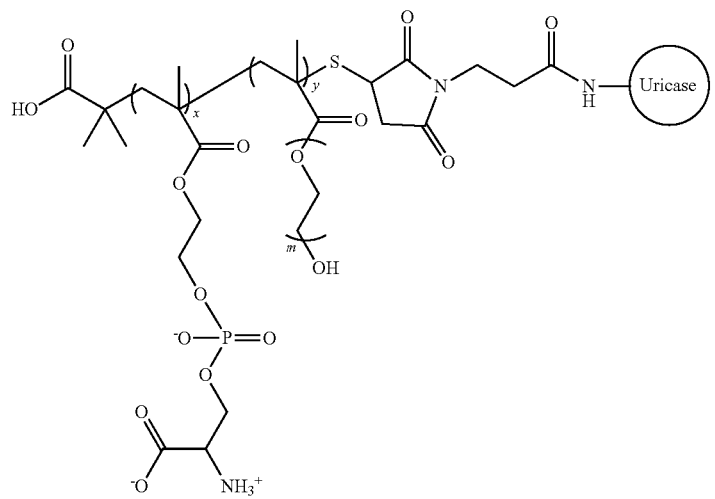
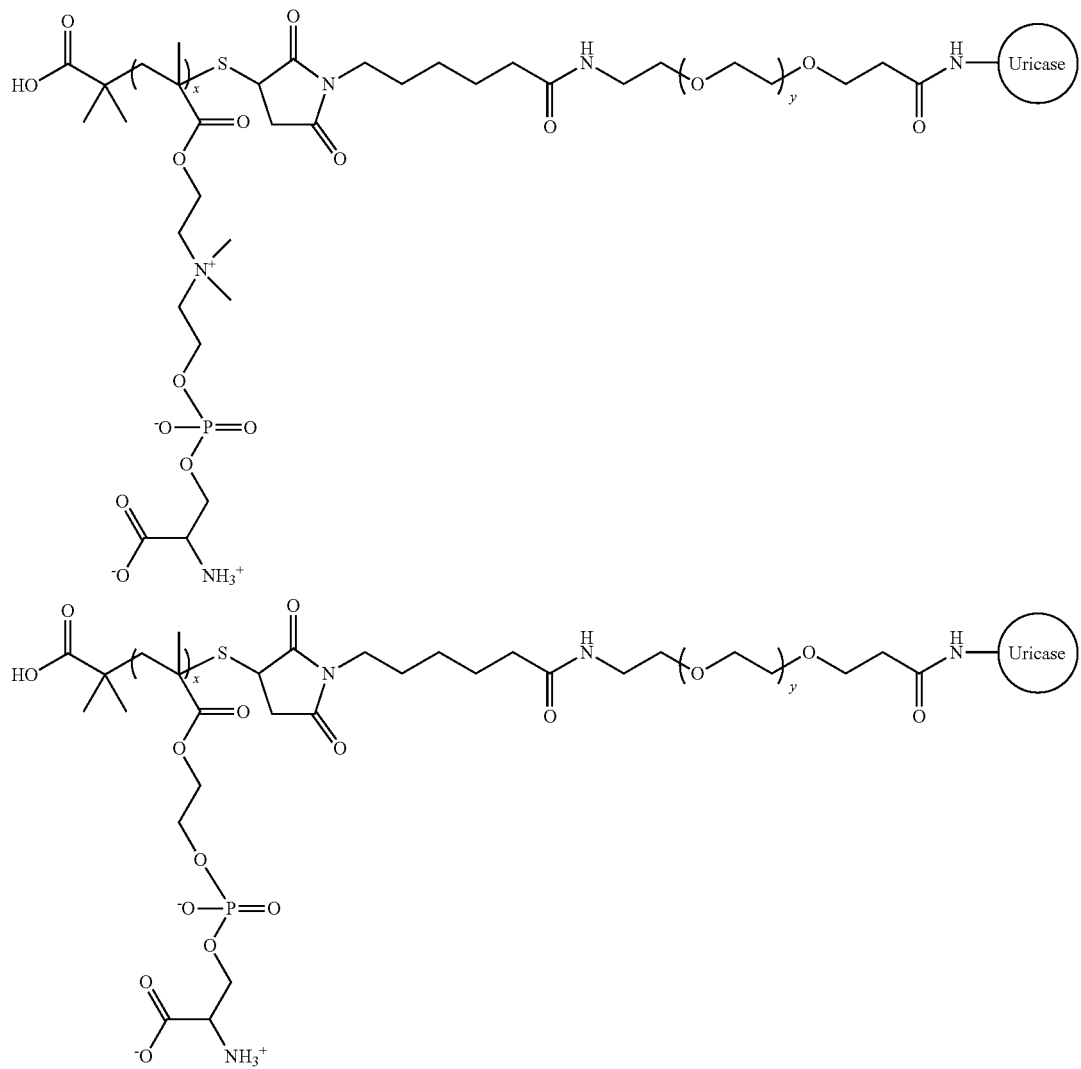

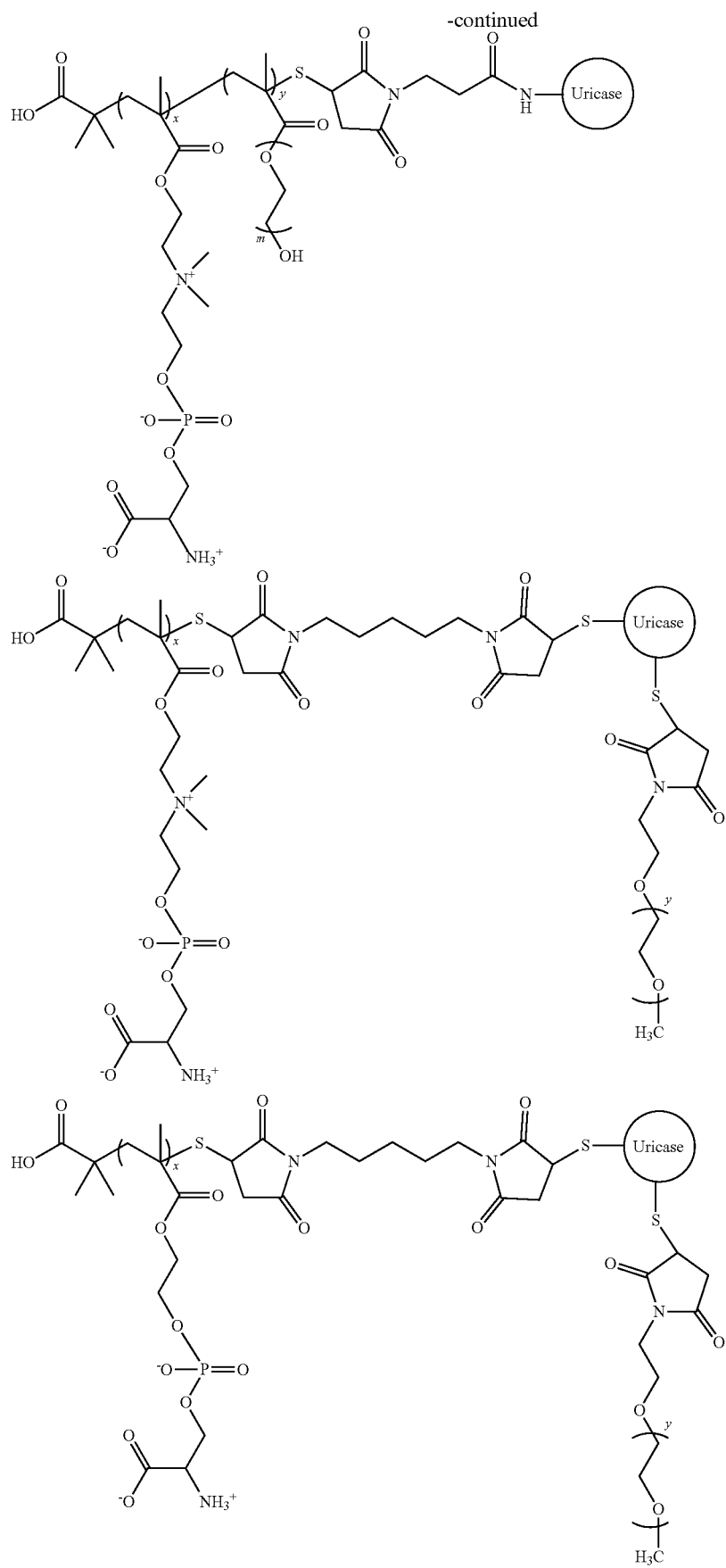

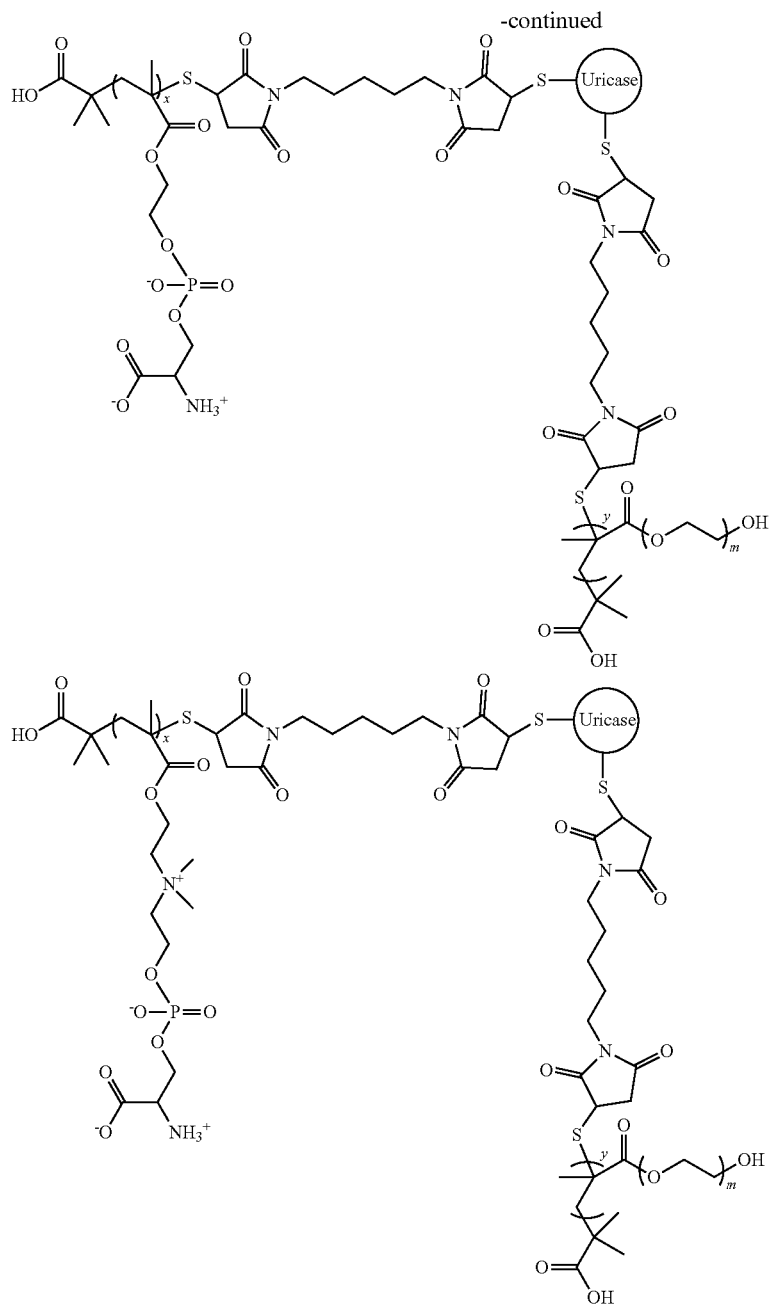

Example 6

Immunogenicity of Representative Neutral PS-PEG Bioconjugates

In this example the immunogenicity of representative neutral PS-PEG bioconjugates is compared to a representative PEG-uricase.

PEG-uricase and PS-mimetic polymer-PEG-uricase at a dose of 25 U/kg body weight is intravenously administered into the rats via the tail vein. The administrations of uricase samples are repeated five times with one week as the time interval between each immunization. At the end of the fifth week (35$^{th}$ day), all the rats are euthanized. The rats are sacrificed and their blood collected through cardiac puncture are handled for direct ELISA test. For ELISA test, while the detection of anti-uricase antibody uses coated uricase as antigen, the detection of anti-PEG antibody requires BSA-PEG conjugates.

As the first step of direct ELISA test, 100 μL antigen solutions (10 μg/mL of protein concentration) prepared in coating buffer (0.1 M sodium carbonate buffer, pH 10.5) are used to coat each well of 96-well plates. After overnight coating at 4° C. overnight, the plates are washed five times using PBS buffer (pH 7.4) to remove the antigen solutions and then filled with blocking buffer (1% BSA solution in 0.1 M Tris buffer, pH 8.0) for 1 hr incubation at room temperature, subsequent to which the blocking buffer is removed. All wells are then washed by PBS buffer for another five times. Subsequently, serial dilutions of rat sera in PBS buffer containing 1% BSA are added to the plates (100 μL/well) for 1 hr incubation at 37° C., subsequent to which the rat sera are removed and all wells are washed five times with PBS buffer. Next, goat anti-rat IgM or IgG (HRP-conjugated, Bethyl Laboratories) as the secondary antibody are added into each well for another 1 hr incubation at 37° C. Subsequently, all the wells are washed five times using PBS buffer before the addition of 100 μL/well HRP substrate 3,3',5,5'-tetramethylbenzidine (TMB; Bethyl Laboratories). The plates are shaken for 15 min, and 100 μL stop solution (0.2 M $H_2SO_4$) is added to each well. Absorbance at 450 (signal) and 570 nm (background) is recorded by a microplate reader. Rat sera naïve to the administration of uricase samples are used as the negative control for all ELISA detections.

The spleens of rats are harvested and the splenocyte is isolated by 100 μm cell strainer (Fisherbrand™). The rat splenocytes from each group are stained with anti-rat Abs to MHCII and CD86 (eBioscience) and then analyzed by flow cytometry. For the test of T cell activation, rat splenocytes from each group are cultured in 12-well plate ($10^6$/well) and re-stimulated with PEG-uricase, and PS-mimetic polymer-PEG-uricase (1 mg/ml) respectively. The splenocytes from each rat are cultured in two wells as parallel groups. After 72 h, the cell culture medium from each well is collected for the quantification of IL-4 using IL-4 Rat ELISA kit (Life Technologies).

Example 7

Immunogenicity of Representative ZPS, Neutral PS, and PC Bioconjugates

In this example the immunogenicity of representative bioconjugates is described. The bioconjugate is a uricase conjugate. The uricase conjugates were prepared by covalently coupling (a) a zwitterionic PS (ZPS) polymer, (b) a neutral, non-zwitterionic (NZPS) polymer, or (c) a phosphatidaylcholine (PC) (MPC) polymer to the uricase surface.

Briefly, AOT (120 mg) and Brij 30 (230 mg) were added to a 20 mL glass vial to which a stir bar was added. The vial was sealed with a Teflon-lined septum cap and purged with dry nitrogen for 10 min. Nitrogen-deoxygenated hexane (5 mL) was then added to the vial under vigorous stirring. For the aqueous phase, uricase (1 mg) was dissolved in HEPES buffer (pH 8.5, 125 μL), to which ZPS monomer (50 mg) were added and dissolved. Dry nitrogen was bubbled through the monomer/protein solution for 2 min, after which the aqueous phase was slowly added to the organic continuous phase dropwise. The vial was sonicated to form a stable microemulsion. A 20% (w/v) solution of APS (10 μL) in Milli-Q water was then added to the emulsion. After 5 min, polymerization was initiated by the addition of TEMED (6 μL) and maintained at 4° C. under rapid magnetic stirring. After the 2-hour reaction, the organic solvent was removed by rotary evaporator and the ZPS-uricase conjugate was precipitated and washed with THF for three times. The ZPS-uricase conjugate was re-suspended in PBS buffer and purified with high resolution size exclusion chromatography (Sephacryl S-500HR) to remove the free uricase. Finally the conjugates were washed and concentrated with PBS (pH 7.4) for three times using a 100-kDa molecular weight cutoff centrifugal filter.

The structures of the conjugates are illustrated schematically below.

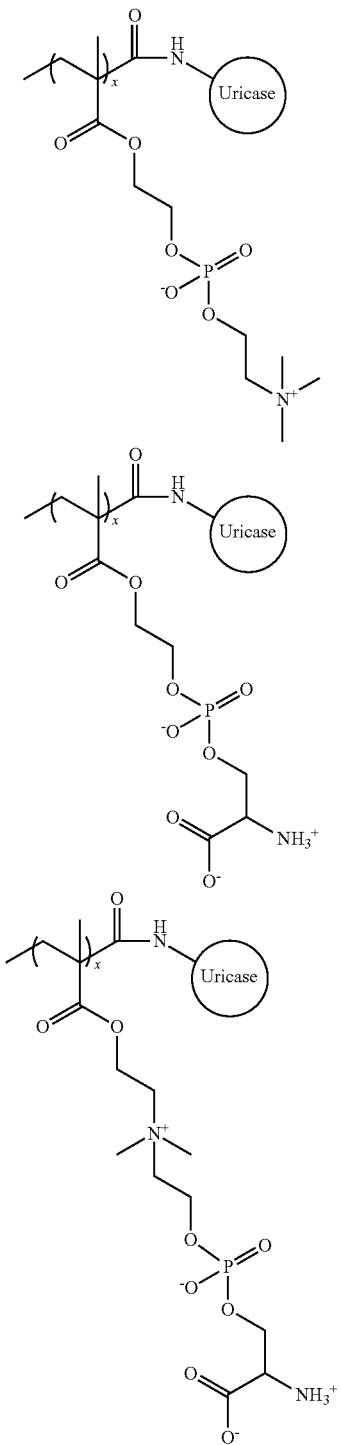

For in vitro immunogenicity study, DC 2.4 dendritic cells ($10^5$/well) were incubated with PBS (blank control), native uricase, ZPS-uricase, NZPS-uricase, MPC-uricase conjugates (2 mU/mL) respectively for 72 hours. At the end of the incubation period, the cells were spun at 300 g for 10 min and the supernatant medium was collected for cytokine (TGF-beta) analysis by ELISA. The cells were harvested and washed twice with ice cold sterile phosphate-buffered saline. Cells were labeled with anti-CD40-FITC or anti-CD80-PE and analyzed using flow cytometry. As shown in FIGS. 3A and 3B, exposure to the native uricase resulted in an increase in the expression of costimulatory marker CD40 and CD80 (FIG. 3A) and thus a reduction in immature dendritic cells (FIG. 3B). In contrast, MPC-uricase, NZPS-uricase, and ZPS-uricase displayed an alleviated effect on stimulating the activation of dendritic cells, among which NZPS-uricase has the least effect, followed by ZPS-uricase. The measurement of TGF-beta, a typical immunosuppressive cytokine marker (FIG. 3C) suggests that while MPC-uricase does not affect the level of TGF-beta, both NZPS-uricase and ZPS-uricase have a phenomenal effect in upregulating the secretion of TGF-beta.

For in vivo immunogenicity study, ZPS-uricase, NZPS-uricase, MPC-uricase conjugates at a dose of 25 U/kg body weight are IV administered into the mice via the tail vein. The administrations of uricase samples are repeated three times with one week as the time interval between each administration. The mouse blood was collected at various time points (0, 6 h, 24 h, 48 h, 72 h) and the retained uricase in blood was estimated by measuring the enzyme activity with Amplex™ uric acid/uricase kit. At the end of three weeks (21st day), all the mice are euthanized. The mice are sacrificed and their blood collected through cardiac puncture are handled for direct ELISA test.

As the first step of direct ELISA test, 100 μL antigen solutions (10 μg/mL of protein concentration) prepared in the coating buffer (0.1 M sodium carbonate buffer, pH 10.5) are used to coat each well of 96-well plates. After overnight coating at 4° C. overnight, the plates are washed five times using PBS buffer (pH 7.4) to remove the antigen solutions and then filled with blocking buffer (1% BSA solution in 0.1 M Tris buffer, pH 8.0) for 1 hr incubation at room temperature, subsequent to which the blocking buffer is removed. All wells are then washed by PBS buffer for another five times. Subsequently, serial dilutions of mouse sera in PBS buffer containing 1% BSA are added to the plates (100 μL/well) for 1 hr incubation at 37° C., subsequent to which the mouse sera are removed and all wells are washed five times with PBS buffer. Next, goat anti-rat IgM or IgG (HRP-conjugated, Bethyl Laboratories) as the secondary antibody is added into each well for another 1 hr incubation at 37° C. Subsequently, all the wells are washed five times using PBS buffer before the addition of 100 μL/well HRP substrate 3,3',5,5'-tetramethylbenzidine (TMB; Bethyl Laboratories). The plates are shaken for 15 min, and 100 μL stop solution (0.2 M $H_2SO_4$) is added to each well. Absorbance at 450 (signal) and 570 nm (background) is recorded by a microplate reader. Mouse sera naïve to the administration of uricase samples are used as the negative control for all ELISA detections. Moreover, the mice spleens were harvested on 21st for the isolation of splenocytes by 100 μm cell strainer (Fisherbrand™). The mice splenocytes from each group were cultured in the presence of native uricase, MPC-uricase, NZPS-uricase or ZPS-uricase for 72 h, and then stained with anti-CD4-PE, anti-CD25-FITC and anti-Foxp3-Percep antibodies for the analysis by flow cytometry.

As shown in FIGS. 4A and 4B and Table 1, uricase conjugated with MPC, an inert zwitterionic polymer, suffers an accelerated blood clearance (ABC) after three administrations.

TABLE 1

Pharmacokinetic parameters after repeated injections.

| Parameters | NZPS uricase (injection) | | ZPS-uricase (injection) | | MPC-uricase (injection) | | Native uricase | |
|---|---|---|---|---|---|---|---|---|
| | 1 | 3 | 1 | 3 | 1 | 3 | 1 | 3 |
| $t_{1/2\alpha}(h)$ | 1.5 | 1.6 | 2.4 | 2.2 | 2.5 | 2.1 | 1.3 | 0.8 |
| $t_{1/2\beta}(h)$ | 15.1 | 15.2 | 27.9 | 27.1 | 30.1 | 23.2 | 11.2 | 8.1 |
| MRT | 17.3 | 18.6 | 36.7 | 35.7 | 40.9 | 28.1 | 9.2 | 3.7 |

The development of anti-uricase or anti-conjugate antibodies (FIGS. 4C and 4D) is accountable for the ABC phenomenon occurred to native uricase and MPC-uricase conjugates. In contrast, both zwitterionic PS (ZPS) polymer and non-zwitterionic PS (NZPS) polymer can suppress the potential immune response elicited by the immunogenic protein carrier (uricase). Such an immunosuppressive effect leads to the absence of anti-conjugate antibodies (FIGS. 4C and 4D) and thus maintain the circulation time of uricase conjugates post to repeated administrations (Table 1). The circulation time of NZPS-uricase is much shorter than that of the ZPS-uricase, indicating that the "eat-me" signal of PS headgroup in NZPS could result in a rapid clearance, which is unfavorable to increase the retention time of proteins in vivo. In contrast, the circulation time of ZPS-uricase is comparable to that of MPC-uricase, evincing that the ZPS, like other zwitterionic materials, prolongs the circulation time of proteins while it also retains the immunosuppressive effect of PS, thus inhibiting the immunogenicity of proteins. This unique property of ZPS makes it particularly suitable for nanoparticles (e.g., protein conjugates, liposomes, micelles, and solid nanoparticles, such as gold, quantum dot, silica, and iron oxide nanoparticles) as its achieves long circulation and low immunogenicity simultaneously. Moreover, the characterization of mouse splenocytes confirmed that NZPS-uricase and ZPS-uricase conjugate could upregulate the expression T-rege cells (FIGS. 4E and 4F), which is accountable for their avoidance of undesirable immune responses.

While illustrative embodiments have been illustrated and described, it will be appreciated that various changes can be made therein without departing from the spirit and scope of the invention.

The invention claimed is:

1. A particle having micro- or nanoscale dimensions, comprising one or more zwitterionic phosphatidylserine polymers coupled to the particle, wherein the one or more zwitterionic phosphatidylserine polymers have repeating units having the formula:

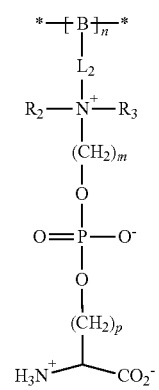

wherein
* indicates the point of attachment of the repeating unit to other repeating units in the polymer or copolymer, or polymer or copolymer terminal groups;
B is a polymer backbone;
$L_2$ is a linker group selected from $-(CH_2)_x-$, $-C(=O)NH(CH_2)_x-$, $-C(=O)O(CH_2)_x-$, $-C(=O)OC(=O)O(CH_2)_x-$, $-(CH_2)_x-O-(CH_2)_x-$, and $-(CH_2)_x-S-S-(CH_2)_x-$, where x at each occurrence is an integer independently selected from 1 to 20;
$R_2$ and $R_3$ are independently selected from the group consisting of hydrogen, $C_1$-$C_{20}$ alkyl, and $C_6$-$C_{12}$ aryl;
m is an integer from 1 to 20;
p is an integer from 1 to 20; and
n is an integer from about 10 to about 500.

2. The particle of claim 1, wherein the particle is a biomolecule.

3. The particle of claim 2, wherein the biomolecule is a protein, a nucleic acid, a glycoprotein, a lipid, or a proteoglycan.

4. The particle of claim 2, wherein the biomolecule is a protein selected from an enzyme, a signaling protein, a haemostasis or a thrombosis protein, a vaccine, a complement system protein, or an antibody or a functional fragment or characteristic portion thereof.

5. The particle of claim 2, wherein the biomolecule is a small molecule therapeutic agent.

6. The particle of claim 1, wherein the particle is a drug delivery vehicle.

7. The particle of claim 1, wherein the particle is a cell, a virus, or a bacterium.

8. The particle of claim 1, wherein the particle is a hydrogel.

9. The particle of claim 1, wherein the particle is a metal, a metal oxide, a ceramic, a synthetic polymer, a natural polymer, a crystal, a semiconductor material, a grapheme, a graphene oxide, an iron oxide, or a silica, or a quantum dot.

10. The particle of claim 1, wherein the one or more zwitterionic phosphatidylserine polymers have repeating units having the formula:

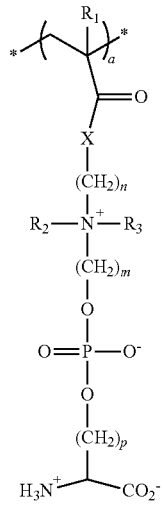

wherein
* indicates the point of attachment of the repeating unit to other repeating units in the polymer or copolymer, or polymer or copolymer terminal groups;

$R_1$ is selected from the group consisting of hydrogen, fluorine, trifluoromethyl, cyano, $C_1$-$C_{20}$ alkyl, and $C_6$-$C_{12}$ aryl;
$R_2$, and $R_3$ are independently selected from hydrogen and $C_1$-$C_6$ alkyl;
X is O or NH,
n is an integer from 1 to 20;
m is an integer from 1 to 20;
p is an integer from 1 to 20; and
a is an integer from about 10 to about 500.

11. A surface of a substrate having one or more zwitterionic phosphatidylserine polymers covalently coupled thereto, wherein the one or more zwitterionic phosphatidylserine polymers have repeating units having the formula:

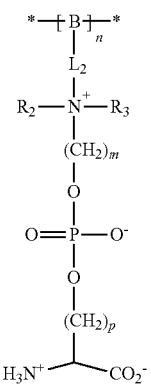

wherein
* indicates the point of attachment of the repeating unit to other repeating units in the polymer or copolymer, or polymer or copolymer terminal groups;
B is a polymer backbone;
$L_2$ is a linker group selected from $-(CH_2)_x-$, $-C(=O)NH(CH_2)_x-$, $-C(=O)O(CH_2)_x-$, $-C(=O)OC(=O)O(CH_2)_x-$, $-(CH_2)_x-O-(CH_2)_x-$, and $-(CH_2)_x-S-S-(CH_2)_x-$, where x at each occurrence is an integer independently selected from 1 to 20;
$R_2$ and $R_3$ are independently selected from the group consisting of hydrogen, $C_1$-$C_{20}$ alkyl, and $C_6$-$C_{12}$ aryl;
m is an integer from 1 to 20;
p is an integer from 1 to 20; and
n is an integer from about 10 to about 500.

12. A monomer having the formula:

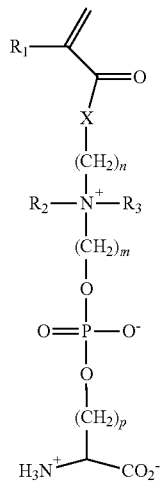

wherein,
$R_1$ is selected from the group consisting of hydrogen, fluorine, trifluoromethyl, cyano, $C_1$-$C_{20}$ alkyl, and $C_6$-$C_{12}$ aryl,
$R_2$, and $R_3$ are independently selected from hydrogen and $C_1$-$C_6$ alkyl, X is O or NH,
n is an integer from 1 to 20,
m is an integer from 1 to 20, and
p is an integer from 1 to 20.

13. A polymer or copolymer having repeating units, wherein one or more repeating units comprise a zwitterionic phosphatidylserine moiety, wherein the one or more zwitterionic phosphatidylserine polymers have repeating units having the formula:

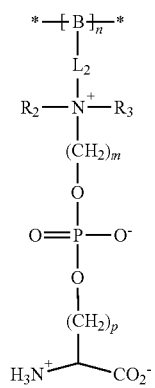

wherein
* indicates the point of attachment of the repeating unit to other repeating units in the polymer or copolymer, or polymer or copolymer terminal groups;
B is a polymer backbone;
$L_2$ is a linker group selected from —$(CH_2)_x$—, —$C(=O)NH(CH_2)_x$—, —$C(=O)O(CH_2)_x$—, —$C(=O)OC(=O)O(CH_2)_x$—, —$(CH_2)_x$—O—$(CH_2)_x$—, and —$(CH_2)_x$—S—S—$(CH_2)_x$—, where x at each occurrence is an integer independently selected from 1 to 20;
$R_2$ and $R_3$ are independently selected from the group consisting of hydrogen, $C_1$-$C_{20}$ alkyl, and $C_6$-$C_{12}$ aryl;
m is an integer from 1 to 20;
p is an integer from 1 to 20; and
n is an integer from about 10 to about 500.

14. A polymer or copolymer of claim 13 having repeating units having the formula:

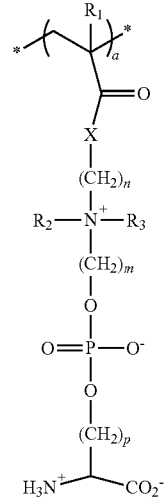

wherein
* indicates the point of attachment of the repeating unit to other repeating units in the polymer or copolymer, or the polymer or copolymer terminal groups;
$R_1$ is selected from the group consisting of hydrogen, fluorine, trifluoromethyl, cyano, $C_1$-$C_{20}$ alkyl, and $C_6$-$C_{12}$ aryl;
$R_2$ and $R_3$ are independently selected from hydrogen and $C_1$-$C_6$ alkyl;
X is O or NH;
n is an integer from 1 to 20;
m is an integer from 1 to 20;
p is an integer from 1 to 20; and
a is an integer from about 10 to about 500.

* * * * *